US006498014B1

(12) United States Patent
Testa et al.

(10) Patent No.: US 6,498,014 B1
(45) Date of Patent: Dec. 24, 2002

(54) MONOCLONAL ANTIBODIES THAT RECOGNIZE ANTIGENS ASSOCIATED WITH TUMOR METASTASIS

(75) Inventors: Jacqueline E. Testa, Spring Valley; James P. Quigley, La Jolla, both of CA (US); Marco Seandel, East Setauket, NY (US)

(73) Assignee: The Research Foundation of State University of NY, Stony Brook, NY (US)

( * ) Notice: Subject to any disclaimer, the term of this patent is extended or adjusted under 35 U.S.C. 154(b) by 0 days.

(21) Appl. No.: 09/499,781

(22) Filed: Feb. 8, 2000

Related U.S. Application Data

(62) Division of application No. 09/333,599, filed on Jun. 15, 1999, now Pat. No. 6,245,898.
(60) Provisional application No. 60/089,226, filed on Jun. 5, 1998, and provisional application No. 60/109,300, filed on Nov. 20, 1998.

(51) Int. Cl.$^7$ ............................................. G01N 33/53
(52) U.S. Cl. ..................... 435/7.1; 435/7.23; 530/387.3; 530/388.85
(58) Field of Search ........................... 435/4, 7.1, 7.23, 435/7.92; 530/387.1, 388.1, 388.8, 388.85, 389.1, 389.7

(56) References Cited

PUBLICATIONS

Information for JCB Contributors 1/1993.*
Paul Fundamental immunology, Raven Press, NY, Chapter 8, p. 242, 1993.*
Brooks et al., The Journal of Cell Biology 122:1351–1359, 1993.*
Harlow E., et al. (1988) "Antibodies, A Laboratory Manual", Cold Spring Harbor Laboratory pp. 31–35, 72–77, 92–94, 96–97, 128–129, and 288.
Berditchevski, F., et al. (1999) "Characterization of Integrin–Tetraspanin Adhesion Complexes: Role of Tetraspanins in Integrin Signaling", *J. Cell Biol.* 146(2):477–492.
Brooks, P.C., et al. (1993) "Substractive Immunization Yields Monoclonal Antibodies that Specifically Inhibit Metastasis", *J. Cell Biol.* 122(6):1351–1359.
Fitter, S., et al. (1995) "Molecular Cloning cDNA Encoding a Novel Platelet–Endothelial Cell Tetra–Span Antigen, PETA–3", *Blood* 86(4):1348–1355.
Fitter, S., et al. (1999) "Transmembrane 4 superfamily protein CD151(PETA–3) associates with $\beta_1$ and $\alpha_{IIb}\beta_3$ integrins in haemopoietic cell lines and modulates cell–cell adhesion", *Biochem J.* 338:61–70.
Fitter, S., et al. (1998) "Characterization of the mouse homologue of CD151 (PETA–3/SFA–1);genomic structure, chromosomal localisation and identification of 2 novel splice forms", *Biochimica et Biophysica Acta* 1398(1):75–85.

Flint, M., et al. (1999) "Characterization of Hepatitis C Virus E2 Glycoprotein Interaction with a Putative Cellular Receptor, CD81", *J. of Virology* 73(8):6235–6244.
Ghannadan, M., et al. (1988) "Phenotypic Characterization of Human Skin Mast Cells by Combined Staining with Toluidine Blue and CD Antibodies", *J. of Investigative Dermatology* 111(4):689–695.
Hasegawa, H., et al. (1998) "SFA–1/PETA–3 (CD151), a Member of the Transmembrane 4 Superfamily, Associates Preferentially with $\alpha_5\beta_1$ Integrin and Regulates Adhesion of Human T Cell Leukemia Virus Type 1–Infected T Cells to Fibronectin", *J. of Immunology* 161(6):3087–3095.
Hasegawa, H., et al. (1997) "Molecular cloning and expression of mouse homologue of SFA–1/PETA–3 (CD151), a member of the transmembrane 4 superfamily", *Biochimica et Biophysica Acta* 1353(2):125–130.
Hasegawa, H., et al. (1997) "Assignment of SFA–1 (PETA–3), a Member of the Transmembrane 4 Superfamily, to Human Chromosome 11p15.5 by Fluorescence in Situ Hybridization", *Genomics* 40: 193–196.
Hasegawa, H., et al. (1996) "SFA–1, a Novel Cellular Gene Induced by Human T–Cell Leukemia Virus Type 1, Is a Member of the Transmembrane 4 Superfamily", *J. of Virology* 70(5):3258–3263.
Hemler, M. E., et al. (1996) "Association of TM4SF proteins with integrins: relevance to cancer", *Biochimica et Biophysica Acta* 1287:67–71.
Maecker, H. T., et al. (1997) "The tetraspanin superfamily:molecular facilitators", *FASEB J.* 11:428–442.
Maeda, H., et al. (1991) "Construction of reshaped human antibodies with HIV–neutralization activity", *Hum. Antibod. Hybridomas* 2:124–134.
Padlan, E. A. (1991) "A Possible Procedure For Reducing The Immunogenicity Of Antibody Variable Domains While Preserving Their Ligan–Binding Properties", *Mol.Immunology* 28(4/5):489–498.
Roberts, J. J., et al. (1995) "Platelet activation induced by murine monoclonal antibody directed against a novel tetra–span antigen", *British J.Haematology* 89:853–860.
Serru, V, et al., (1999) "Selective tetraspan–integrin complexes (CD81/$\alpha4\beta1$, CD151/$\alpha3\beta1$, CD151/$\alpha6\beta1$) under conditions disrupting tetraspan interactions", *Biochemical Journal* 340(Pt1):103–111.

(List continued on next page.)

*Primary Examiner*—Sheela Huff
*Assistant Examiner*—Larry R. Helms
(74) *Attorney, Agent, or Firm*—Scully, Scott, Murphy & Presser

(57) ABSTRACT

This invention provides tumor metastasis-inhibiting monoclonal antibodies, mAb 41-2, mAb 50-6 and mAb 1A-5. The antigen recognized by mAb 50-6 and mAb 1A-5 has been identified as the PETA-3 antigen. The antigen recognized by mAb 41-2 has been identified as a novel tumor metastasis-associated antigen. Compositions and methods are provided that are useful for treating and diagnosing metastatic tumors.

3 Claims, 26 Drawing Sheets

OTHER PUBLICATIONS

Sincock, P. M., et al. (1997) "Localization of the Transmembrane 4 Superfamily (TM4SF) Member PETA–3 (CD151) in Normal Human Tissues: Comparison with CD9, CD63, and α5β1 Integrain", *J. Histochemistry & Cytochemistry* 45(4):515–525.

Sincock, P. M., et al. (1999) "PETA–3/CD151, a member of the transmembrane 4 superfamily, is localised to the plasma membrane and endocytic system of endothelial cells, associates with multiple integrins and modulates cell function", *J. of Cell Science* 112:833–844.

Sugiura, T., et al. (1999) "Function of α3β1–Tetraspanin Protein Complexes in Tumor Cell Invasion. Evidence for the Role of the Complexes in Production of Matrix Metalloproteinase 2 (MMP–2)", *J. Cell Biol.* 146(6):1375–1389.

Tanyel, F. C., et al. (1999) "Inguinal Hernia Revisited Through Comparative Evaluation of Peritoneum, Processus Vaginalis, and Sacs Obtained From Children With Hernia, Hydrocele, and Undescended Testis", *J. of Pediatric Surgery* 34(4):552–555.

Testa, J. E., et al. (1999) "Eukaryotic Expression Cloning with an Antimetastic Monoclonal Antibody Identifies a Tetraspanin (PETA–3/CD151) as an Effector of Human Tumor Cell Migration and Metastasis", *Cancer Research* 59:3812–3820.

Testa, J. E., et al. (1999) "Eukaryotic expression cloning with an antimetastatic monoclonal antibody identifies a tetraspanin (PETA–3/CD151) as an effector of human tumor cell migration and metastasis" (Abstract), Molecular Aspects of Metastasis (An AACR Special Conference in Cancer Research), Sep. 22–26, 1999, Snowmass, Colorado. (Approx 180–200 participants; the work was presented as a poster and as an oral presentation).

Testa, J. E., et al. (1997) "Identification and Characterization of Metastasis–Associated Antigens"(Abstract), *Congress on In Vitro Biology*, Meeting of the Society for In Vitro Biology, Jun. 14–18, 1997, Washington, D.C. V–10.

Testa, J. E., et al. (1998) "Eukaryotic Expression Cloning of a Metastasis–Associated Antigen in Human Tumor Cells" (Abstract), VII International Congress of the Metastasis Research Society, Oct. 7–10, 1998. San Diego, California. (Approx 300–400 participants; the work was presented as a poster and as an oral presentation).

Yáñez–Mó, M., et al. (1998) "Regulation of Endothelial Cell Motility by Complexes of Tetraspan Molecules CD81/TAPA–1 and CD151/PETA–3 with α3β1 Integrin Localized at Endothelial Lateral Junctions", *J. Cell Biology* 141(3):791–804.

Yauch, R. L., et al. (1998) "Highly Stoichimetric, Stable, and specific Association of Integrin α3β1 with CD151 Provides a Major LInk to Phosphatidylinositol 4–Kinase, and May Regulate Cell Migration", *Molecular Biology of the Cell* 9(10):2751–2765.

\* cited by examiner

ATCCACTAGTAACGGCCGCCAGTGTGGTGGAATTCGAGTCCTGGGGAGCTTCTGTCCTCCACCTGTCCTGCAGAGGAGTCGTT

TCCAGCCCGGCTGCCCCAGGATGGGTGAGTTCAACGAGAAGAAGACAACATGTGGCACCGTTTGCCTCAAGTACCTGCTG
                  START CODON

TTTACCTACAATTGCTGCTTCTGGCTGGCTGGCCTGGCCTGTGTCATGGCAGTGGGCATCTGGACGCTGGCCCTCAAGAGTGA

CTACATCAGCCTGCTGGCCTCAGGCACCTACATCCTGGTTGGCCACTGTCGTCATGGTGA

CTGGGGTCTTGGGCTGCTGCGCCACCTTCAAGGAGCGTCGGAACCTGCTGCGCCTGTACTTCATCCTGCTCCTCATCATC

TTTCTGCTGGAGATCATCGCTGGTATCCTCGCCTACCACCAGCTGAACACGGAGCTCAAGGAGAACCTGAA

GGACACCATGACCAGGCGCTACCAGTCGGGCCATGAGCCTGTGTGACCAGCTGCAGCAGGAGTTCC

ACTGCTGTGGCAGCAACAACTCACAGAGACTGGCGAGACAGTGAGTGGATCCCGCTCACAGGAGCCGGTGGCCGTGTGGTC

CCAGACAGCTGCTGCAAGACGGTGGTGCTCTTTGTGGACAGACCATGCCTCCAACATCTACAAGGTGGAGGGCGG

CTGCATCACCAAGTTGGAGACCTTCATCCAGGAGCACCTGAGGGTCATTGGGCTGTGGGATCGGCATTGCCTGTGTGC

AGGTCTTTGGCATGATCTTCACGTGCTGCCTGTACAGGAGTCTTCAAGCTGGAGCACTACTGACCCTGCCT
                                                      STOP CODON

Figure 1A

\* \* \* SEQUENCE \* \* \*

```
GGAGCTTCTG TCCACCTGTC CTGCAGAGGA GTCGTTTCCA GCCCGGCTGC CCCAGGATG    59
                                                             M

GGT GAG TTC AAC GAG AAG AAG ACA ACA TGT GGC ACC GTT TGC CTC AAG    107
 G   E   F   N   E   K   K   T   T   C   G   T   V   C   L   K

TAC CTG CTG TTT ACC TAC AAT TGC TGC TTC TGG CTG GCT GGC CTG GCT    155
 Y   L   L   F   T   Y   N   C   C   F   W   L   A   G   L   A

GTC ATG GCA GTG GGC ATC TGG ACG CTG GCC CTC AAG AGT GAC TAC ATC    203
 V   M   A   V   G   I   W   T   L   A   L   K   S   D   Y   I

AGC CTG CTG GCC TCA GGC ACC TAC CTG GCC ACA GCC TAC ATC CTG GTG    251
 S   L   L   A   S   G   T   Y   L   A   T   A   Y   I   L   V

GTG GCG GGC ACT GTC GTC ATG GTG ACT GGG GTC TTG GGC TGC TGC GCC    299
 V   A   G   T   V   V   M   V   T   G   V   L   G   C   C   A

ACC TTC AAG GAG CGT CGG AAC CTG CTG CGC CTG TAC TTC ATC CTG CTC    347
 T   F   K   E   R   R   N   L   L   R   L   Y   F   I   L   L

CTC ATC ATC TTT CTG CTG GAG ATC ATC GCT GGT ATC CTC GCC TAC GCC    395
 L   I   I   F   L   L   E   I   I   A   G   I   L   A   Y   A

TAC TAC CAG CAG CTG AAC ACG GAG CTC AAG GAG AAC CTG AAG GAC ACC    443
 Y   Y   Q   Q   L   N   T   E   L   K   E   N   L   K   D   T

ATG ACC AAG CGC TAC CAC CAG CCG GGC CAT GAG GCT GTG ACC AGC GCT    491
 M   T   K   R   Y   H   Q   P   G   H   E   A   V   T   S   A

GTG GAC CAG CTG CAG CAG GAG TTC CAC TGC TGT GGC AGC AAC AAC TCA    539
 V   D   Q   L   Q   Q   E   F   H   C   C   G   S   N   N   S

CAG GAC TGG CGA GAC AGT GAG TGG ATC CGC TCA CAG GAG GCC GGT GGC    587
 Q   D   W   R   D   S   E   W   I   R   S   Q   E   A   G   G

CGT GTG GTC CCA GAC AGC TGC TGC AAG ACG GTG GTG GCT CTT TGT GGA    635
 R   V   V   P   D   S   C   C   K   T   V   V   A   L   C   G

CAG CGA GAC CAT GCC TCC AAC ATC TAC AAG GTG GAG GGC GGC TGC ATC    683
 Q   R   D   H   A   S   N   I   Y   K   V   E   G   G   C   I

ACC AAG TTG GAG ACC TTC ATC CAG GAG CAC CTG AGG GTC ATT GGG GCT    731
 T   K   L   E   T   F   I   Q   E   H   L   R   V   I   G   A

GTG GGG ATC GGC ATT GCC TGT GTG CAG GTC TTT GGC ATG ATC TTC ACG    779
 V   G   I   G   I   A   C   V   Q   V   F   G   M   I   F   T

TGC TGC CTG TAC AGG AGT CTC AAG CTG GAG CAC TAC TGA CCC TGC CTT    825
 C   C   L   Y   R   S   L   K   L   E   H   Y
```

Figure 1B

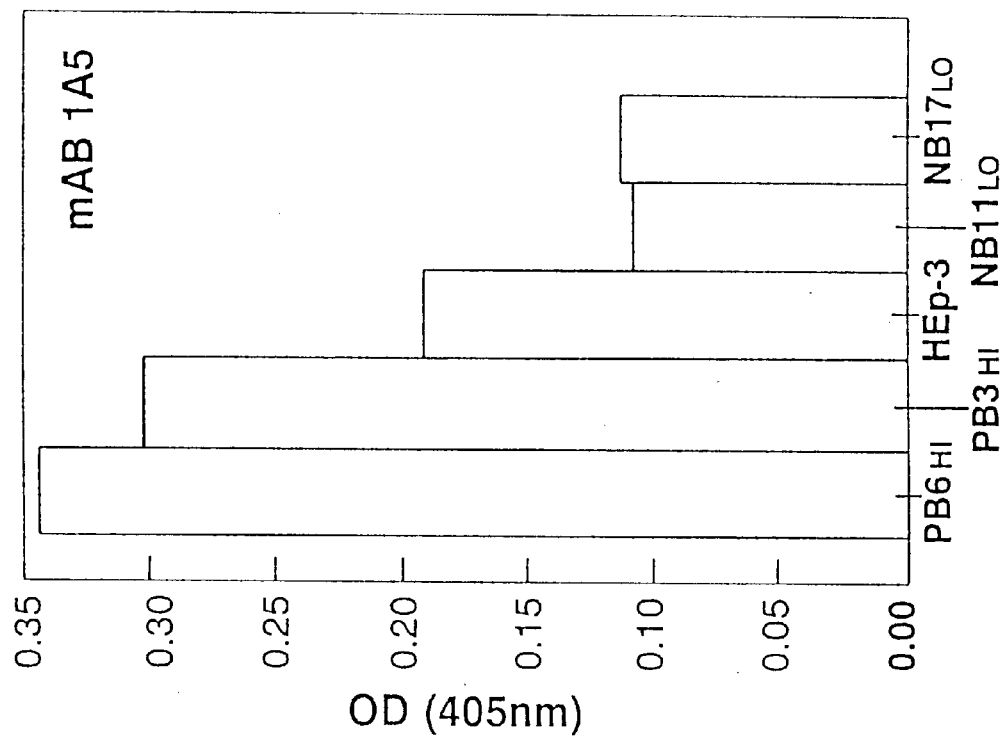
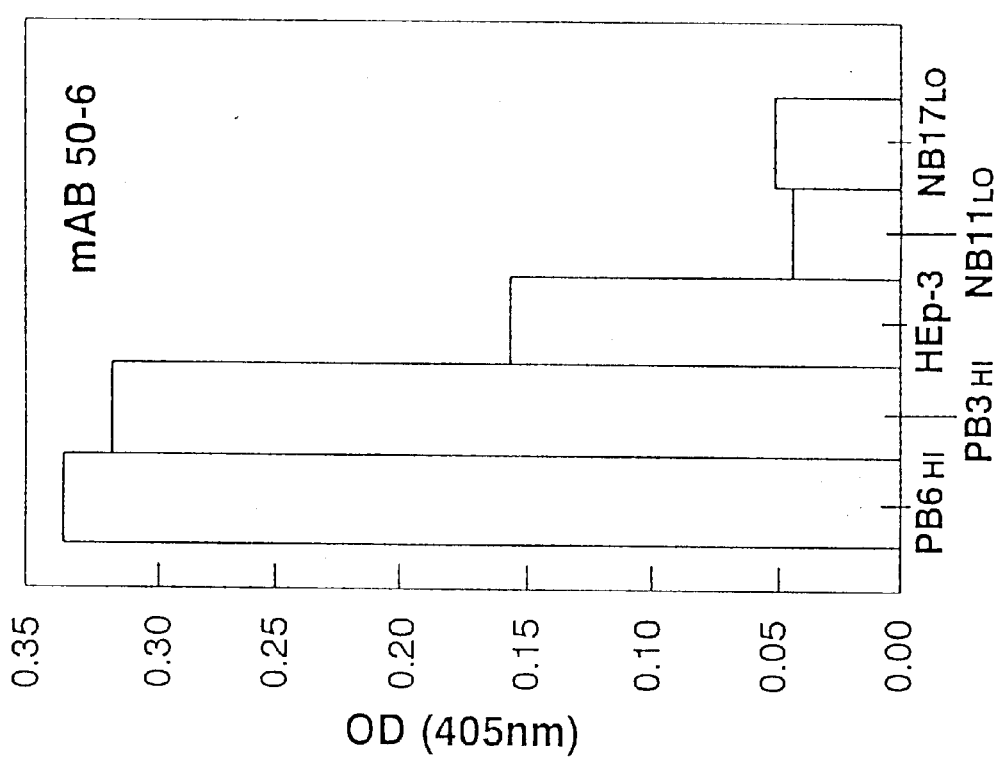
Figure 12A
Figure 12B

```
human  (  1)  MGEFNEKKTTCGTVCLKYLLFTYNCCFWLAGLAVMAVGIWTLALKSDYIS
mouse  (  1)  MGEFNEKKaTCGTVCLKYLLFTYNCCFWLAGLAVMAVGIWTLALKSDYIS human  ( 51)  LLASGTYLATAYILVVAGTVVMTGVLGCCATFKERRNLLRLYFILLLII
mouse  ( 51)  LLASsTYLATAYILVVAGvVVMTGVLGCCATFKERRNLLRLYFILLLII human  (101)  FLLEIIAGILAYAYYQQLNTELKENLKDTMTKRYHQPGHEAVTSAVDQLQ
mouse  (101)  FLLEIIAGILAYvYYQQLNTELKENLKDTMvKRYHQsGHEQvSSAVDKLQ human  (151)  QEFHCCGSNNSQDWRDSEWIRSQEAGGRVVPDSCCKTVVALCGQRDHASN
mouse  (151)  QEFHCCGSNNSQDWqDSEWIRSqEAdsRVVPDSCCKTmVAgCGkRDHASN human  (201)  IYKVEGGCITKLETFIQEHLRVIGAVGIGIACVQVFGMIFTCCLYRSLKL
mouse  (201)  IYKVEGGCITKLETFIQEHLRVIGAVGIGIACVQVFGMIFTCCLYRSLKL human  (251)  EHY
mouse  (251)  EHY
```

Figure 20

```
PETA-3  (113)  AYYQQLNTELKENLKDTMTKRYHQPGHEAVTSAVDQLQQEFHCCGSNNSQ
CD9     (111)  SHKDEVIKEVQEFYKDTYNKLKT--KDEPQRETLKAIHYALNCCGLAGGV
CD63    (105)  VFRDKVMSEFNNNFRQQMENYP---KNNHTASILDRMQADFKCCGAANYT

PETA-3  (163)  DWRDSEWIRSQEAGGRVVPDSCCKTVVALCGQRDHASNIYKVEGGCITKL
CD9     (159)  EQF-------------ISDICPKKDVLRTF--------TVKSCPDAI
CD63    (152)  DWEKIPSMSKNR------VPDSCCINVTVGCG--INFNEKAIHKEGCVEKI

PETA-3  (213)  ETFIQEHLR
CD9     (185)  KEVFDNKFH
CD63    (196)  GGWLRKNVL
```

Figure 21

MONOCLONAL ANTIBODIES THAT RECOGNIZE ANTIGENS ASSOCIATED WITH TUMOR METASTASIS

CROSS REFERENCE TO RELATED APPLICATIONS

This application is a divisional of U.S. application Ser. No. 09/333,599, filed on Jun. 15, 1999, now U.S. Pat. No. 6,245,898, which claims priority from U.S. Provisional Applications No. 60/089,226, filed on Jun. 15, 1998, and No. 60/109,300, filed on Nov. 20, 1998.

This invention was made in the course of work under grants 1R01CA656600 and 1R01CA60800 sponsored in part by the National Institute of Health.

FIELD OF THE INVENTION

This invention relates to tumor metastasis-inhibiting monoclonal antibodies as well as antigens that are recognized by such antibodies. Compositions and methods are provided that are useful for treating and diagnosing metastatic tumors.

DESCRIPTION OF RELATED ART

Malignant tumors shed cells which migrate to new tissues and create secondary tumors; a benign tumor does not generate secondary tumors. The process of generating secondary tumors is called metastasis and is a complex process in which tumor cells colonize sites distant from the primary tumor. Tumor metastasis remains the major cause of deaths in cancer patients, yet the molecular mechanisms underlying tumor cell dissemination are not clearly understood. There is a need to identify new molecules that are functionally involved in cancer cell dissemination in order to gain insights into the basics of metastatic spread, and to identify novel prognostic indicators and/or therapeutic targets.

Metastasis is a multi-step process in which tumor cells must detach from the primary tumor, invade the cellular matrix, penetrate through blood vessels, thus enter the circulatory system (intravasate), arrest at a distant site, exit the blood stream (extravasate), and grow. See, e.g., G. L. Nicolson (1982) *Biochim. Biophis. Acta.* 695: 113–176; G. L. Nicolson and G. Poste (1983) *In. Rev. Exp. Pathol.* 25: 77–181; G. Poste and I. J. Fidler (1980) *Nature* 283: 139–145; and E. Roos (1984) *Biochim. Biophis. Acta.* 738: 263–284. Given the complexity of the process, it is likely that there are a number of genes which mediate tumor cell metastasis. Indeed, the metastatic phenotype has been correlated with expression of a variety of proteins, including proteases, adhesion molecules, and the like. However, evidence that a given protein is directly involved in dissemination is often lacking, or difficult to prove. L. A. Liotta and W. Stetler-Stevenson (1989) *J. Natl. Cancer Inst.* 81: 556–557.

The human epidermoid carcinoma, HEp-3, provides a unique model system with which to detect and characterize those genes which effect metastatic dissemination. HEp-3 cells, propagated by serial passage on the chick chorioallantoic membrane (CAM), are both tumorigenic and spontaneously metastatic (T+M+). L. Ossowski and E. Reich (1980a) *Cancer Res.* 40: 2300–2309. However, when cells are grown continuously in vitro, they readily form primary tumors, but progressively become non-metastatic (T+M–) with time. L. Ossowski and E. Reich (1980b) *Cancer Res.* 40: 2310–2315. With prolonged cultivation in vitro, they eventually become non-tumorigenic also (T–M–). Loss of metastatic ability is reversible. T+M– cells carried on the CAM for two to three passages regain the ability to form spontaneous metastases. Thus, by altering growth conditions, the metastatic potential of these cells can be manipulated by the investigator.

Human urokinase-type plasminogen activator (uPA) was shown to be directly involved in dissemination of HEp-3, as spontaneous metastasis of HEp-3 cells in the chick embryo was inhibited by antibodies that were specific for human uPA. L. Ossowski and E. Reich (1983b) *Cell* 35: 611–619. Subsequently, it was observed that inhibition of uPA activity blocked infiltration of the CAM mesenchyme by individual HEp-3 cells. L. Ossowski (1988a) *Cell* 52: 321–328. However, active uPA appeared to be required for tumor cell intravasation but not extravasation. L. Ossowski (1988a). Thus, some other factor(s) must be also involved in HEp-3 dissemination. J. P. Quigley et al. (1988) *Ciba Foundation Symposium* 141: 22–47 and Brooks et al. (1993) *J. Cell Biol.* 122 (6): 1351–1359 describe the generation of monoclonal antibodies (mAbs), using "subtractive immunization", which recognize cell surface antigens expressed on HEp-3 cells and inhibit tumor metastasis in the CAM model.

Angiogenesis is the growth of new blood vessels from pre-existing vessels. Endothelial cells which line the vessel walls degrade the surrounding basement membrane and migrate into the surrounding connective tissue. The migrating endothelial cells form cords, which eventually develop lumena and become patent vessels. Angiogenesis plays a vital role in normal physiological processes (e.g., would healing, ovulation). Inappropriate angiogenesis is involved in a number of pathological processes, such as cancer metastasis, diabetic retinopathy, etc.

The present invention has generated monoclonal antibodies by subtractive immunization, which inhibit tumor metastasis and/or angiogenesis. The antigens that are recognized by such monoclonal antibodies have been identified as well.

SUMMARY OF THE INVENTION

One embodiment of the present invention provides tumor metastasis-inhibiting monoclonal antibodies 41-2 and 50-6. Functional derivatives and fragments of such monoclonal antibodies are also contemplated by the present invention.

Another embodiment of the present invention provides hybridoma cell lines 41-2 (ATCC #PTA-226) and 50-6 (ATCC #PTA-227), which produce mAb 41-2 and mAb 50-6, respectively.

Another embodiment of the present invention provides the antigens recognized by the monoclonal antibodies of the present invention, more particularly, the target antigen of mAb 41-2.

Another embodiment of the present invention is directed to antibodies raised against the target antigen of mAb 41-2, as well as antibodies raised against the target antigen of mAb 50-6.

Another embodiment of the present invention is directed to nucleic acid molecules coding for the target antigen of mAb 41-2 or a portion thereof. Expression vector and host cells are also contemplated by the present invention.

In a further aspect of the present invention, pharmaceutical compositions are provided.

A pharmaceutical composition of the present invention can include the PETA-3 antigen or a portion thereof, or the antigen recognized by mAb 41-2 or a portion thereof.

A pharmaceutical composition of the present invention can also include an antibody directed against PETA-3 or the target antigen of mAb 41-2.

A preferred pharmaceutical composition of the present invention includes a tumor-metastasis-inhibiting antibody. Preferred tumor-metastasis-inhibiting antibodies include mAb 41-2, mAb 50-6 and mAb 1A-5.

A further aspect of the invention provides methods of diagnosing metastatic tumors in a subject by detecting the expression of at least one of the metastasis-associated antigens identified by the present invention, including the PETA-3 antigen or the antigen recognized by mAb 41-2. The detection can be accomplished by using an antibody or a nucleic acid probe.

Another embodiment of the present invention provides methods of treating a metastatic tumor in a subject by administering to the subject a therapeutically effective amount of a tumor metastasis-inhibiting antibody of the present invention.

Another embodiment of the present invention provides methods of treating a metastatic tumor in a subject by administering to the subject a therapeutically effective amount of an antisense molecule of the PETA-3 gene or the gene encoding the target antigen of mAb 41-2.

In still another embodiment, the present invention is directed to methods of treating aberrant PETA-3-dependent angiogenesis in a subject by administering a therapeutically effective amount of an angiogenesis-inhibiting antibody directed against PETA-3 or a functional derivative of such antibody.

BRIEF DESCRIPTION OF THE DRAWINGS

FIG. 1A depicts the nucleotide sequence (SEQ ID NO: 1) of a cDNA clone isolated in expression cloning using mAb 50-6;

FIG. 1B depicts the encoded amino acid sequence (SEQ ID NO: 2) of the cDNA clone isolated in expression cloning using mAb 50-6.

FIG. 2A HEp-3 cells incubated with mAb 50-6;

FIG. 2B HEp-3 cells incubated with normal mouse IgG;

FIG. 2C COS cells transiently transfected with PETA-3 cDNA and incubated with mAb 50-6;

FIG. 2D COS cells transiently transfected with PETA-3 cDNA and incubated with normal mouse IgG;

FIG. 2E COS cells transiently transfected with vector (pcDNA I) alone and incubated with mAb 50-6. A 20 μm bar is shown in the lower right of each panel.

FIG. 3A: Western blot of HEp-3 cell lysate (10 μg; lane 1) lysates from control (COS/pcDNA I; 20 μg; lane 2) and PETA-3-transfectants (COS/PETA-3; 20 μg; lane 3) probed with mAb 50-6.

FIG. 3B: Western blot of HEp-3 cell lysate (0.5 μg; lane 1) and lysates from control (COS/pcDNA I; lane 2; 2.5 μg) and PETA-3 transfectants (COS/PETA-3; lane 3; 2.5 μg) probed with mAb 1A5. In both FIG. 3A and FIG. 3B the signals were visualized with a peroxidase-conjugated goat anti-mouse IgG by chemiluminescence. PETA-3 is identified with an arrow at 29 kD. Molecular weight markers, in kilodaltons (kD) are shown to the right.

FIGS. 12A–12G depict the effects of PETA-3/CD151 expression on HeLa cell migration. HeLa cells were co-transfected with the cloned PETA-3/CD151 cDNA and pSV2neo. Controls were co-transfected with pcDNA I and pSV2neo. Two PETA-3 over-expressing clones ($PB6_{HI}$ and $PC3_{HI}$) and two control clones ($NB11_{LO}$ and $NB17_{LO}$) were selected.

FIGS. 12A–12B depict the amount of cell surface PETA-3 expressed by the HeLa transfectants and HEp-3 cells, determined by whole-cell ELISA on fixed, non-permabilized cells and expressed as the optical density (OD) of the chromogen at 405 nm.

FIG. 12C depicts the in vitro growth rates of the HeLa transfectants, determined by plating $2 \times 10^4$ cells into each of two wells in a 24-well plate. At the times indicated, the cells were trypsinized and counted. Results are reported as number of cells per well.

FIGS. 12D–12G depict the inhibition of HeLa migration by mAb 50-6 and mAb 1A5. Experiments were conducted in triplicate.

FIG. 20 depicts the alignment of the amino acid sequences of human and mouse PETA-3/CD151. Amino acids are indicated by the standard IUPAC one-letter code. Putative transmembrane domains are underlined. The extracellular loops are double underlined. Substitutions are indicated with a vertical line. Non-conservative amino acid substitutions in the human sequence are shaded in gray.

FIG. 21 depicts the alignment of the amino acid sequences of the large extracellular loops of human PETA-3, CD9 and CD63. Amino acids are indicated by the standard IUPAC one-letter code. Amino acids shaded in gray are the non-conservative substitutions identified in the human sequence when compared to the mouse PETA-3 homologue.

DETAILED DESCRIPTION OF THE INVENTION

Figure 2A:
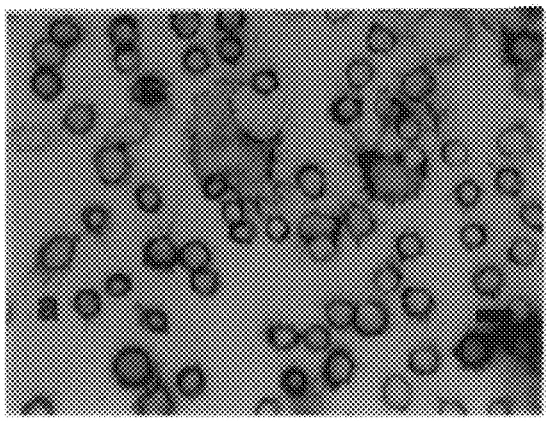
FIGS. 2A–2E depict the immunocytochemical localization of PETA-3 on HEP-3 cells and COS transfectants. Cells were plated onto poly-lysine-coated glass cover slips, fixed 24 hours later, and then immunostained with mAb 50-6 or normal mouse IgG. Signals were detected with horseradish peroxidase-conjugated goat anti-mouse IgG and chloronaphthol. All images were photographed with transmitted light.

The present invention relates to isolated monoclonal antibodies that inhibit tumor metastasis. The present invention further relates to tumor metastasis-associated antigens recognized by such monoclonal antibodies, the nucleic acid molecules encoding such antigens, as well as other antibodies raised against such antigens. The present invention also provides pharmaceutical compositions and methods useful for diagnosing and treating metastatic cancers.

One embodiment of the present invention is directed to monoclonal antibodies 41-2 and 50-6.

According to the present invention, mAb 41-2, and mAb 50-6 inhibit metastasis of tumors, including tumors of a tissue origin of the epiderm, breast, lung, liver, kidney, epithelial, thyroid, leukemic, pancreatic, endometrial, ovarian, cervical, skin, colon or lymphoid tissues. The present invention has also demonstrated that mAb 50-6 inhibits growth factor-induced angiogenesis.

The metastasis inhibitory effects of these monoclonal antibodies can be attributed to binding of the mAbs to specific tumor metastasis-associated antigens and interfering with the function of such antigens in tumor metastasis.

The term "tumor metastasis-associated antigen" as used herein, includes antigens that are specifically expressed in metastatic tumor cells and essentially not expressed in non-metastatic tumor cells or normal cells; antigens that are overexpressed in metastatic tumor cells relative to non-metastatic tumor cells or normal cells; and antigens that are expressed similarly in metastatic tumor cells and non-metastatic tumor cells, but are required for the process of tumor metastasis.

As demonstrated by the present invention, both the antigen recognized by mAb 41-2 and the antigen recognized by mAb 50-6 are expressed at a substantially higher level on metastatic HEp-3 cells than on non-metastatic HEp-3 cells. The antigen recognized by mAb 41-2 is also expressed on metastatic human breast carcinoma cells at a substantially higher level than on less metastatic human breast carcinoma cells or normal human mammary epithelial cells. In addition, the antigen recognized by mAb 50-6 is expressed at a substantially higher level on human mammary metastatic carcinoma cells than on normal human mammary cells.

Functional derivatives of the instant monoclonal antibodies are also contemplated by the present invention.

"Functional derivatives" refer to antibody molecules or fragments thereof that are derived from the instant monoclonal antibodies and that have retained the antigen specificity of the instant monoclonal antibodies. Examples of functional derivatives include Fab, Fab', F(ab')$_2$ of the present mAbs, single chain antibodies, humanized antibodies and the like.

A single-chain antibody (SAb) is created by fusing together the variable domains of the heavy and light chains using a short peptide linker, thereby reconstituting an antigen biding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. (1990) *J. Biol. Chem.*, 265: 18615; Chaudhary et al. (1990) *Proc. Natl. Acad. Sci.*, 87: 9491; U.S. Pat. No. 4,946,778 to Ladner et al.; and U.S. Pat. No. 5,359,046 to Capon et al.

The murine monoclonal antibodies of the present invention can be humanized to reduce the immunogenicity for use in humans. One approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication #PCT/US86/02269 (published May 7, 1987); Liu et al., *Proc. Natl. Acad. Sci. USA* 84: 3439–3443 (1987); Sun et al., *Proc. Natl. Acad. Sci. USA* 84: 214–218 (1987); Better et al., *Science* 240: 1041–1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

Humanized antibodies can be made using a second approach, i.e., to construct a reshaped human antibody, which has been described in, e.g, Maeda et al., *Hum. Antibod. Hybridomas* 2: 124–134, 1991, and Padlan, *Mol. Immunol.* 28: 489–498, 1991.

The monoclonal antibodies of the present invention can be prepared from the culture supernatant of hybridoma cell lines 41-2 (deposited with the American Type Culture Collection, 10801 University Blvd., Manassas, Va. 20110-2209, on Jun. 15, 1999, ATCC #PTA-226) and 50-6 (deposited with the American Type Culture Collection on Jun. 15, 1999, ATCC #PTA-227), respectively. Such hybridoma cell lines form another embodiment of the present invention.

The hybridoma cell line of the present invention have been generated by the "subtractive immunization" procedure. Briefly, recipient mice were first inoculated with non-metastatic human epidermoid carcinoma HEp-3 cells, followed by injections of an immunosuppressive (tolerizing) agent cyclophosphamide. The tolerizing agent suppressed the immune response in the recipient mice towards dominant immundeterminants present on the non-metastatic tumor cells. The tolerized mice were then immunized with metastatic HEp-3 cells to generate an immune response to antigenic determinants present on the metastatic tumor cells. A boosting injection with metastatic tumor cells was made afterwards. Subsequently, monoclonal antibody-producing spleen cells from the immunized mice were isolated and fused with the immortalized murine myeloma cell line NSO to produce hybridomas. The procedure for making hybridomas is well known in the art and can be found in, e.g., Harlow, E. and Lane, D., *Antibodies: A Laboratory Manual*, Cold Spring Harbor Press, 1988. The supernatants of the cultured hybridomas were tested in a whole-cell ELISA assay for differential reactivity toward metastatic tumor cells over non-metastatic tumor cells, which cells were used in the subtractive immunization procedure. In the whole-cell ELISA assay, tumor cells were fixed but not permeablized, such that only cell surface antigens were accessible for binding by antibodies in the hybridoma supernatants. Hybridomas producing antibodies which recognized antigenic determinants that were expressed on metastatic tumor cells at a substantially higher level than on non-metastatic cells were identified. Clones 50-6 and 41-2 were obtained after limiting dilution.

The hybridomas of the present invention can be grown in various tissue culture flasks, yielding supernatants with variable concentrations of antibodies. Hybridoma cells can be injected into animals to produce inflammatory ascites. Antibody-containing ascites can be harvested 8–12 days after intraperitoneal injection. The ascites contain a higher concentration of antibodies, but include both monoclonals and immunoglobulins from the animal.

Monoclonal antibodies in the hybridoma supernatant or in the ascites can be purified by a variety of conventional protein purification methods, for example, affinity chromatography. Alternatively, hybridoma supernatant or the ascites can be used directly in place of the monoclonal antibodies under certain circumstances. Those skilled in the art can determine whether purification of the monoclonal antibodies is required for a particular use.

Another embodiment of the present invention is directed to the antigens recognized by the monoclonal antibodies of the present invention, i.e., the target antigens.

More particularly, the present invention has identified and isolated the target antigen of mAb 50-6. Such antigen has been determined to be identical to a protein known as PETA-3/CD151. PETA-3/CD151 has not been associated with tumor metastasis or angiogenesis prior to the present invention.

Furthermore, the present invention provides the isolated target antigen of mAb 41-2.

According to the present invention, the target antigen of mAb 41-2 is associated with tumor metastasis. Such antigen has been found to be expressed on the surface of metastatic tumor cells, e.g., metastatic mammary carcinoma, at a substantially higher level than on the surface of non-metastatic tumor cells or normal cells. By "substantially higher" it means at least about 20% higher, preferably, at least about 25% higher, more preferably, at least about 35% higher.

Such antigen has been substantially purified from metastatic Hep-3 cell lysate using mAb 41-2. The antigen appears as a single band on a SDS-PAGE under both reducing and non-reducing conditions with an approximate Mw of about 180 kD. The immun-purified antigen was subjected to Edman degradation, and the subsequent sequencing analysis revealed a N-terminal sequence of FEIALPRESQITVLQ(I)KXGT (SEQ ID NO: 3) (residue #15 is either Q or I; residue 17 has not been determined). Comparison of this partial amino acid sequence with known sequences in the NCBI database has revealed that this antigen has not been previously identified.

Another embodiment of the present invention is directed to antibodies raised against the target antigen of mAb 41-2 and antibodies raised against the target antigen of mAb 50-6. According to the present invention, such antibodies do not include mAb 1A-5 (produced by hybridoma 1A-5 and described by Brooks et al., *JCB* 122: 1351, 1993), 11B1.G4 or 14A2.H1 (the latter two described by Fitter et al., Blood 4: 1348–1355, 1995). However, the present invention contemplates pharmaceutical compositions which include mAb 1A-5 and methods for diagnosing or trating metastatic tumors by using mAb 1A-5.

The antigen, preferably substantially purified, can be injected, alone or with adjuvant, into an animal to raise antibodies. Polyclonal antibodies can be purified from the serum of the immunized animal. Monoclonal antibodies can be prepared from hybridomas which are produced by fusing the antibody-producing lymphocytes from the immunized animal and an immortal cell line. Procedures for raising and preparing antibodies are well known in the art and can be found in, e.g., Harlow, E. and Lane, D., *Antibodies: A Laboratory Manual*, Cold Spring Harbor Press, 1988.

Functional derivatives and fragments of antibodies raised against the target antigen of mAb 41-2 are also contemplated by the present invention.

Another embodiment of the present invention is directed to nucleic acid molecules coding for the target antigen of mAb 41-2 or a portion thereof.

"A portion" of an antigen as used herein, refers to a peptide fragment of a sufficient length to be antigenic. Generally speaking, the peptide fragment consists of at least 7 or 8 amino acids.

Nucleic acid molecules coding for the target antigen of mAb 41-2 can be obtained by a variety of well known methods. For example, degenerate oligonucleotides can be synthesized based on the partial amino acid sequence of the antigen, FEIALPRESQITVLQ(I)KXGT (SEQ ID NO: 3). Such oligonucleotides can be used to screen a cDNA library made from metastatic tumor cells. Alternatively, mAb 41-2 can be used to screen the encoding gene by, e.g., expression cloning. Expression cloning is well known in the art and is also described in Example 2 relating to the isolation of the target antigen of mAb 50-6.

In another embodiment, nucleotide sequences encoding the target antigen of mAb 41-2 or a portion thereof, have been inserted into an expression vector for production of the antigen or the portion thereof.

According to the present invention, a desired nucleotide sequence can be inserted into a selected vector in an operable linkage to a promoter. For expression in a eukaryotic cell, viral vectors are preferred, e.g., a retroviral, adenoviral, or herpes simplex viral vectors. Yeast vectors are also contemplated. For expression in a prokaryotic cell, phage vectors are preferred, such as a λ phage vector. Baculovirus-based vectors are also useful for recombinant production of large amounts of a protein or portions thereof (O'Reilly et al., *Baculovirus Expression Vectors: A laboratory Manual*, pp. 107–122, CRC Press, Boca Raton, Fla., 1992).

The present invention also contemplates host cells transformed with the above-described expression vector. The host cell lines which can be employed include, but are not limited to, eukaryotic cells, e.g., COS cells such as COS-7, CHO cells such as CHO-1, NIH 3T3 cells, yeast cells such as strains of *Saccharomyces* and *Pichia patoris*, insect cells such as *Spodoptera frugiperda*; and prokaryotic cells, e.g., strains of *E. coli*, strains of Pseudomonas such as *Pseudomonas aeruginosa* or strains of Bacillus.

Recombinant expression allows production and purification of large amounts of the target antigen or a portion thereof, which can be used to raise antibodies, which, in turn, can be used for diagnosing and treating metastatic tumors. In addition, recombinantly produced proteins in large quantity permits large scale screening of therapeutic drugs for treating metastatic tumors.

A further aspect of the invention is directed to pharmaceutical compositions.

A pharmaceutical composition of the present invention can include PETA-3 or a portion thereof, the antigen recognized by mAb 41-2 or a portion thereof, or combinations thereof. Such pharmaceutical compositions can be used as immunogens to raise antibodies in a laboratory animal, or as vaccines to provoke immune responses in a recipient subject which facilitate the elimination of the metastatic tumor cells from the recipient subject.

A pharmaceutical composition of the present invention can also include an antibody directed against the PETA-3 antigen or the target antigen of mAb 41-2, functional derivatives of such antibodies, or combinations thereof.

Preferred antibodies to be used in pharmaceutical compositions include those antibodies that inhibit tumor metastasis, e.g., mAb 41-2, mAb 50-6 and mAb 1A-5. Inhibition of tumor metastasis can be determined by a number of assays, such as the migration assay, the invasion assay or the chick CAM assay as described in the Examples hereinafter.

The pharmaceutical compositions of the present invention can include other substances such as cytokines, adjuvants and pharmaceutically acceptable carriers. As used herein, a pharmaceutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art.

A further aspect of the invention is directed to methods of diagnosing metastatic tumors in a subject by detecting the expression of at least one of the metastasis-associated antigens identified by the present invention, i.e., the PETA-3 antigen or the antigen recognized by mAb 41-2.

"Metastatic tumors" as used in the present invention include both tumors at the primary site capable of metastasizing and metastasized tumors at a secondary site. Such metastatic tumors can be of a tissue origin of the lung, liver, kidney, mammary gland, epithelial, thyroid, leukemic, pancreatic, endometrial, ovarian, cervical, skin, colon and lymphoid tissues.

A "subject" as used herein refers to a mammalian subject, including humans, dogs, monkeys, cows and the like, with the exception of mice.

The expression of a tumor metastasis-associated antigen can be detected by using an antibody directed towards such antigen. Both polyclonal antibodies and monoclonal antibodies can be employed. Preferred antibodies for use in diagnosis include mAb 41-2, mAb 50-6 and mAb 1A-5.

A sample is taken from the subject, e.g., a biopsy specimen taken from tissue suspected of having a metastatic tumor. Generally, the sample is treated before an assay is performed. Assays which can be employed include ELISA, RIA, EIA, Western Blot analysis, immunohistological staining and the like. Depending upon the assay used, the antigens or the antibodies can be labeled by an enzyme, a fluorophore or a radioisotope. See, e.g., Coligan et al. *Current Protocols in Immunology*, John Wiley & Sons Inc., New York, N.Y. (1994); and Frye et al., *Oncogen* 4: 1153–1157, 1987.

The treatment of the sample may vary depending on the assay that is used to detect an antigen. For example, cells of tissue biopsy can be lysed and the cell lysates are used in e.g., Western Blot analysis. For assays such as the Whole Cell ELISA assay, cells can be washed with, e.g., PBS, and then fixed with 0.25% glutaraldehyde in PBS before the assay.

The expression of a tumor metastasis-associated antigen can also be detected by using a nucleic acid probe, e.g., probes that hybridize to the mRNA of a tumor-metastasis antigen, PETA-3 or the target antigen of mAb 41-2.

A PETA-3 nucleic acid probe can be made from any region of PETA-3 RNA or DNA. A probe for detecting the mRNA of the target antigen of mAb 41-2, can be made based on the partial amino acid sequence of such antigen, i.e., SEQ ID NO: 3. In order to produce a detectable signal, the probe is generally at least about 14 nucleotides, and labeled with either an enzyme (such as horse radish peroxidase, alkaline phosphatase, glucose oxidase and β-galactosidase), a fluorophore or a radioisotope.

Detection of the expression of an antigen with a nucleic acid probe can be achieved by a variety of hybridization procedures which are well known in the art. For example, mRNA can be extracted from tissue specimen and analyzed in, e.g., Northern Blot analysis. Alternatively, in situ hybridization procedure can be employed, in which lysis of cells and isolation of RNA are not necessary. See, e.g., *Current Protocols in Molecular Cloning* (Ausubel et al., John Wiley & Sons, New York).

The expression of an antigen detected by using any of the above-described methods, is compared with the expression of the same antigen in the normal part of the tissue. A substantial increase in the level of expression of at least one of the PETA-3 antigen or the target antigen of mAb 41-2, when compared with the expression in the normal tissue, is indicative of a metastatic tumor. By "a substantial increase" it means an increase of at least about 20%, preferably, at least about 25%, more preferably, at least about 35%.

A further aspect of the invention is directed to methods of treating metastatic tumors.

By "treating a metastatic tumor", it means that the metastasis of the tumor is prevented, delayed, or inhibited.

"Metastatic tumors" as used in the present invention include both tumors at the primary site capable of metastasizing and metastasized tumors at a secondary site. Such metastatic tumors can be of a tissue origin of the lung, liver, kidney, mammary gland, epithelial, thyroid, leukemic, pancreatic, endometrial, ovarian, cervical, skin, colon and lymphoid tissue.

A "subject" which can be treated can be any mammalian subject, including humans, dogs, monkeys, cows and the like, with the exception of mice.

One embodiment of the present invention provides methods of treating a metastatic tumor in a subject by administering to the subject a therapeutically effective amount of a tumor metastasis-inhibiting antibody of the present invention.

Tumor metastasis-inhibiting antibodies of the present invention have been described hereinabove. Preferred tumor metastasis-inhibiting antibodies include mAb 41-2, 50-6 and 1A-5, as well as functional derivatives of such mAbs.

Another embodiment of the present invention provides methods of treating a metastatic tumor in a subject by administering to the subject a therapeutically effective amount of an antisense molecule of the PETA-3 gene or the gene encoding the target antigen of mAb 41-2.

An antisense DNA can have at least about 10 nucleotides, preferably, at least about 15 or 17 nucleotides, more preferably, at least about 50 nucleotides. The antisense DNA is preferably inserted into an expression vector in an operable linkage to a promoter which can effect the transcription of the antisense RNA. Any of the well-known gene therapy vectors, such as retroviral, adenoviral, adeno-associated viral, herpes simplex viral vectors, can be used for practicing the methods of the present invention.

A tumor metastasis-inhibiting antibody or an antisense molecule can be administered alone or together with a pharmaceutically acceptable carrier. A pharmaceutically acceptable carrier includes all solvents, such as fats, oils, water, saline solutions, lipids, liposomes, resins, binders, fillers, dispersion media, cell culture media, and the like, or combinations thereof, that are non-toxic to the recipient subject.

In accordance with the present invention, the active ingredients can be combined with the carrier in any convenient and practical manner, e.g., by solution, suspension, emulsification, admixture, encapsulation, absorption and the like, and if necessary, by shaping the combined compositions into pellets or tablets. Such procedures are routine for those skilled in the art.

Dosages of a compound (i.e., an antibody or an antisense molecule) to be therapeutically effective depend on the disease state and other clinical factors, such as weight and condition of the subject, the subject's response to the therapy, the type of formulations and the route of administration. The precise dosage of a compound to be therapeutically effective can be determined by those skilled in the art. As a general rule, the therapeutically effective dosage of a compound can be in the range of about 0.5 $\mu$m to about 2 grams per unit dosage form. A unit dosage form refers to physically discrete units suited as unitary dosages for mammalian treatment: each unit containing a pre-determined quantity of the active material calculated to produce the desired therapeutic effect in association with any required pharmaceutical carrier. The methods of the present invention contemplate single as well as multiple administrations, given either simultaneously or over an extended period of time.

The administration of a tumor metastasis-inhibiting antibody or an antisense molecule may be carried out in any convenient manner, including by aerosol inhalation, injection, ingestion, transfusion, implantation or transplantation. Preferably, the antibodies of the present invention are administered to a patient by subcutaneous (s.c.), intraperitoneal (i.p.), intra-arterial (i.a.), or intravenous (i.v.) injection.

In still another embodiment, the present invention is directed to methods of treating an aberrant PETA-3-dependent angiogenesis in a subject by administering a therapeutically effective amount of an angiogenesis-inhibiting antibody directed against PETA-3 or a functional derivative of such antibody.

The present invention has demonstrated that mAb 50-6 inhibits PETA-3-dependent growth-factor induced angiogenesis, in particular, bFGF-induced angiogenesis. By the same assay, one skilled in the art can readily determine whether an antibody directed against PETA-3 can inhibit angiogenesis. Such angiogenesis-inhibiting antibodies, including mAb 50-6, as well as the functional derivatives thereof, can be used in the methods of treating an aberrant PETA-3-dependent angiogenesis in a subject.

According to the present invention, "an aberrant PETA-3-dependent angiogenesis" include abnormal growth of blood vessels as occurring in patients with hemangiomas, arthritis, ocular neovascularization or the like, which is dependent on the function of PETA-3. According to the present invention, one example of an aberrant PETA-3-dependent angiogenesis is aberrant growth factor-induced angiogenesis, which may be induced by growth factors such as fibroblast growth factor, angiogenin, transforming growth factor $\alpha$, transforming growth factor $\beta$, GCSF, vascular endothelial growth factor, among others.

By "treating an aberrant PETA-3-dependent angiogenesis", is meant that the function of PETA-3 is inhibited by the antibody and the aberrant angiogenesis is prevented or inhibited.

An angiogenesis-inhibiting antibody can be administered as any other antibody described herein. The amount of antibody to be administered that is therapeutically effective depends on the disease state and other clinical factors, such as weight and condition of the subject, the subject's response to the therapy, the type of formulations and the route of administration. The precise dosage of an antibody to be therapeutically effective can be determined by those skilled in the art. As a general rule, the therapeutically effective dosage of a compound can be in the range of about 0.5 $\mu$g to about 2 grams per unit dosage form. A unit dosage form refers to physically discrete units suited as unitary dosages for mammalian treatment: each unit containing a predetermined quantity of the active material calculated to produce the desired therapeutic effect in association with any required pharmaceutical carrier. The methods of the present invention contemplate single as well as multiple administrations, given either simultaneously or over an extended period of time.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

The present invention is further illustrated by the following examples.

EXAMPLE 1

Materials and Methods
Materials

Human breast adenocarcinoma cells MDA-MB 231, MDA-MB 468 and MDA-MB 361 were obtained from American Type Culture Collection (Rockville, Md.). HEp-3 cells were maintained as monolayer cultures and were obtained from solid HEp-3 tumors that were serially passaged on the chorioallantoic membranes (CAMs) of chick embryos as described by Ossowski et al., *Cancer Res.* 40: 2300–2309 (1980) and Ossowski et al., *Cancer Res.* 40: 2310–2315 (1980). The metastatic variant of HEp-3 cells, $M^+$ HEp-3, was cultured for 25 d or less before use. The nonmetastatic variant, $M^-$ HEp-3, was maintained in culture for at least 60–80 d before use. Cells were maintained in DMEM (GIBCO BRL, Gaithersburg, Md.) supplemented with 10% FBS (Hyclone, Logan, Utah), sodium pyruvate, and pen/strep (Sigma Chem. Co., St. Louis, Mo.). All cells were grown in a humidified 5% $CO_2$ atmosphere at 37° C. in 100-mm tissue culture plates (Falcon, Becton Dickinson Labware, Lincoln Park, N.J.).

Fertilized COFAL-negative eggs were obtained from SPAFAS (Norwich, Conn.) and incubated at 37° C. with 60% humidity until use for chick embryo metastasis assays.

Whole Cell ELISA

Subconfluent monolayer cultures of HEp-3 cells, as well as various other cell types, were washed 3× in sterile PBS, removed with nonenzymatic cells dissociation solution, washed in sterile PBS and resuspended in DMEM containing 10% FBS. Cells were added ($2\times10^4/0.1$ ml/well) to 96 well tissue culture plates and allowed to attach for 24–36 h in a humidified atmosphere of 5% $CO_2$ at 37° C. Cells were washed 3× with PBS and fixed with 0.25% glutaraldehyde in PBS (0.1 ml/well) for 10 min. The plates were washed 3× with PBS, blocked with 1.0 M glycine, pH 8.1 (0.1 ml/well) for 2 h at room temperature, washed 3× with PBS and used directly or stored in 0.1% sodium azide in PBS at 4° C. Stored plates were washed 3× with PBS (no azide) just before assay.

The washed, cell-coated wells were blocked with DMEM containing 10% FBS (0.2 ml/well) overnight at 4° C. The primary antibody (hybridoma supernatants or purified mAbs) or the control antibody (normal mouse IgG) was added to the wells (50 μl/well) at a concentration of 1 μg/ml and incubated for 2 h at room temperature. ELISA plates were washed 3 times with PBS containing 0.5% BSA, and then incubated with a horseradish peroxidase (HRP)-conjugated goat anti-mouse IgG (dilution 1:100 in 1% BSA/PBS) (Sigma Chemical Co., St. Louis, Mo.) for 1 h at room temperature. The plates were washed and 100 μl of the substrate, o-phenylene diamine was added to each well. After incubation for 30 min at 37° C., the ELISA plates were read at 405 nm on a Titer Tek Multiscan plate reader, and the amount of chromophore generated from the substrate was quantitated. Nonspecific binding was determined using preimmune sera or normal mouse IgG (Cappel, Organon Teknika, Durham, N.C.) and subtracted from the experimental samples. ELISA ratios were calculated as follows: ($OD_{405}$ $M^+$HEp-3/$OD_{405}$ $M^-$HEp-3).

Western Blot Analysis

Cells were grown to confluence in 100-mm tissue culture plates and washed 3× with PBS. Whole cell lysates were prepared by the addition of 1 ml of lysis buffer (0.1 M Tris pH 8.0 and 1.0% Triton-100 supplemented with a protease inhibitor mixture including 5 mM EDTA, 20 μg/ml Leupeptin, 30 μg/ml TPCK, 20 μg/ml SBTI and 20 U/ml Aprotinin). The lysates were incubated with agitation for 10 min at 4° C. and centrifuged at 3,000 g for 10 min to remove detergent insoluble materials. Lysates having about 20 μg proteins were electrophoresed through either a 10% or 7.5% SDS-PAGE gel under nonreducing conditions. The proteins were transferred onto nitrocellulose membranes. The blots were blocked with 5% non-fat milk, incubated with either mAbs or normal mouse IgG at 4° C. overnight, and washed 4× with 0.1% Tween-20 in PBS for 15 min. Peroxidase-conjugated goat anti-mouse IgG (Sigma Chemical Co., St. Louis, Mo.) was added as secondary antibody. The immunoblots were washed and then developed with the chemiluminescence ECL system (Amersham International, UK) per manufacturer's protocol.

EXAMPLE 2

Isolation of Monoclonal Antibodies 41-2, 50-6 and 1A5

MAb 41-2, mAb 50-6 and mAb 1A5 were generated by a process called "subtractive immunization" in the following manner (see also Brooks et al., *J. Cell. Biol.* 122: 1351–1359, 1993).

C57 BL6 female mice, 6–8 weeks old and 16–18 grams, were obtained from Charles River (Montreal, Quebec). On day 1, subconfluent cultures of $M^-$ HEp-3 cell line were washed three times with sterile PBS and harvested by incubation with 3 ml of nonenzymatic cell dissociation solution (Sigma Chem. Co., St. Louis, Mo.) for 1 min. Cells were resuspended in sterile PBS ($4\times10^6$ cells/ml) and $2\times10^6$ cells were inoculated i.p. into mice. On days 2 and 3, mice were injected i.p. with 200 mg/kg cyclophosphamide (Sigma Chem. Co., St. Louis, Mo.) in sterile PBS. As a tolerizing (immunosuppressive) agent, Cyclophosphamide suppressed the immune response towards dominant immundeterminants present on the tumor cells. On day 15, sera were collected and analyzed in the whole cell ELISA assay for reactivity for $M^-$ HEp-3 cells. On day 18, $M^+$ HEp-3 cells were harvested in the same manner as described above for $M^-$ HEp-3 cells and $2\times10^6$ cells were inoculated i.p. into the mice. On day 39, mice received an i.p. boost of $3\times10^6$ $M^-$ HEp-3 cells. On day 42, sera were collected and analyzed for reactivity toward the $M^+$ HEp-3 cells in the whole cell ELISA. On day 43, the mouse with the greatest $M^+/M^-$ ratio was sacrificed for the production of hybridomas. Variations of the above-described subtractive immunization (S.I.) protocol included the time cyclophosphamide was given, either at 120 and 96 h before the $M^-$HEp-3 cells or 1 and 24 h after the $M^-$HEp-3 cells. A control protocol was performed that was exactly the same as the S.I. protocol except that no cyclophosphamide was given.

Hybridomas were produced according to the standard methods (Worthington et al., *Br. J. Haematol.* 74: 216, 1990). Briefly, the spleens and accessory lymph nodes were removed, washed and fused (4:1 spleen to myeloma) with murine myeloma cell line NSO. The cells were plated ($2.5 \times 10^4$ cells/0.1 ml HAT medium/well) in 96 well tissue culture plates (Falcon, Becton Dickinson Labware). Culture supernatants were screened by the whole cell ELISA and hybridomas from each of the immunization protocols were cloned by soft agar and limiting dilution. Each positive hybridoma was cloned twice. The hybridomas producing antibodies which recognized $M^+$ cells over $M^-$ cells by a factor of 2-fold or higher were selected for further characterization and testing in the metastasis assay.

Monoclonal antibodies were purified from the hybridoma conditioned media as follows. The hybridoma conditioned medium was centrifuged at 3,000 g for 30 min, concentrated 10× with an Amicon Stirred Cell Concentrator (Amicon, Beverly, Mass.) and filtered through a 0.22-$\mu$m filter (Acrodisc, Gelman Sciences, Ann Arbor, Mich.). The concentrated conditioned medium was applied to a protein G Sepharose column (Pharmacia LKB Biotechnology, Piscataway, N.J.) connected to a FPLC (Pharmacia LKB Biotechnology). MAbs were eluted with 0.1 M glycine (pH 3.0). Purified mAbs were immediately neutralized with 1.0 M Tris, pH 9.0, dialyzed against PBS and stored at −20° C.

EXAMPLE 3

Identification of the Target Antigens
The Target Antigen of mAb 41-2
mAb 41-2 was used in a large-scale immunoprecipitation to isolate sufficient amounts of the antigen from Triton X-100 lysates of HEp-3 cells for amino acid sequencing. The immunoprecipitate was resolved by SDS-PAGE under reducing conditions, and following transfer of the resolved proteins to Immobilon-P, a Ponceau-stainable band was observed at 180 kDa (the mobility of the 180 kDa metastasis-associated antigen does not change under reducing conditions). In duplicate immunoblots, the 180 kDa protein was immunostained with mAb 41-2, but not with normal mouse IgG or with secondary antibody alone. The immunopurified metastasis-associated antigen was subjected to Edman degradation and a partial amino acid sequence, FEIALPRESQITVLQ(I)KXGT (SEQ ID NO: 3) was obtained from the amino terminus (residue #15 is either Q or I; residue 17 has not been determined). Comparison of this partial amino acid sequence with known sequences in the NCBI database revealed that this antigen has not been previously cloned.
The Target Antigen of mAbs 50-6 and 1A5
mAbs were used to screen a HEp-3 cDNA expression library in the following manner. Highly metastatic HEp-3 cells were generated by continuous passage on the CAM. Primary HEp-3 cell cultures were established from the metastatic CAM tumors as described by Testa (*Cancer Res.* 52: 5597–5603, 1992). The cultured HEp-3 cells were trypsinized and passaged at confluence. After two weeks of culture in vitro, poly A+ RNA was isolated from the monolayer HEp-3 cells using the FastTrack mRNA isolation system (Invitrogen) according to the manufacturer's instructions, and stored at −80° C. At the same time, cells from a parallel culture plate were tested in the CAM assay system to confirm their metastatic behavior prior to construction of the cDNA library.

A custom-made M+ HEp-3 cDNA library was constructed in the eukaryotic expression vector pcDNA I (Invitrogen Corp., San Diego, Calif.) using the poly A+ RNA isolated as described above. pcDNA I is a plasmid useful for expression cloning in eukaryotic cells. pcDNA I contains the SV40 and polyoma origins of replication which permit episomal replication when transfected into eukaryotic cells expressing the large T antigen (e.g., COS monkey cells), thus allowing high copy numbers of the introduced cDNAs in the cells and accumulation of high levels of the encoded antigens. In addition, the encoded proteins are glycosylated by the COS cells and directed to their normal subcellular location.

First strand synthesis from the HEp-3 RNA was primed with a Not "T" primer, a modified oligo dT primer with an internal Not I site which allowed unidirectional cloning of the cDNA into BstX/NotI-cut pcDNA I. A library size of $3.84 \times 10^6$ primary recombinants was obtained. Of 10 randomly picked clones, all contained inserts. The average insert size was 1.5 kb, with a range of 1.0 kb to 3.1 kb.

A portion of the library was grown in liquid culture. Plasmid DNA was purified with a QIAGEN Plasmid Kit (QIAGEN) following the manufacturer's instructions. Such purified plasmid DNA was used for transfection into COS cells. Twenty-four hours prior to transfection, $0.7 \times 10^6$ COS cells were plated in 100 mm dishes. The cells were transfected with the plasmid DNA (10 $\mu$g/dish) using the calcium phosphate method (Wigler et al., *Proc. Natl. Acad. Sci. USA* 76: 1373–1376, 1979) with a glycerol shock 6 hours after application of the DNA. Seventy-two hours after transfection, the cells were detached from the plates with Non-enzymatic Cell Dissociation Solution (Sigma) and washed twice in calcium- and magnesium-free PBS containing 10 mM EDTA and 5% FBS (PBS/EDTA/FBS). The cells were resuspended in PBS/EDTA/FBS containing 0.4 $\mu$g/ml of mAb 50-6, and incubated on ice for 1 hr. The suspension was centrifuged, the supernatant was removed, and the cells were washed once in PBS/EDTA/FBS.

COS cells expressing the HEp-3 antigen recognized by mAb 50-6 were isolated by immunological panning according to the method of Wysocki and Sato (*Proc. Natl. Acad. Sci. USA* 75: 2844–2848, 1978). Briefly, antibody-incubated cells were resuspended in PBS/EDTA/FBS and 3 ml of the suspension was added to a 100 mm bacteriological dish previously coated with goat anti-mouse IgG. The plates were incubated on a level surface at room temperature for 2 hr, after which the plates were gently washed with 3×10 ml of PBS/EDTA/FBS. Because of the presence of EDTA in the solution, attachment of the COS cells with the panning plate was mediated via antibody interactions. Episomal plasmid DNA was recovered from the selected COS cells by Hirt lysis (Hirt, *J. Mol. Biol.* 26: 365–369, 1967), and rescued by electroporation into highly competent bacteria. The resulting bacterial colonies were scraped off the plates and grown in liquid culture, from which culture plasmids were isolated with the QIAGEN Plasmid Kit. COS cells were subjected to a second round of transfection, incubation with mAb 50-6, panning, Hirt lysis and plasmid rescue as described above. Bacterial transformants were expanded in culture and the plasmids isolated for a third round of transfection. Plasmids were rescued from the transfected COS cells, amplified in bacterial culture and size selected on an agarose gel. COS cells were transfected with the size-selected plasmid fractions and immunostained with mAb 50-6. One positive fraction was identified. Bacteria were transformed with plasmids isolated from this fraction, and mini-prep plasmid DNA was isolated from individual colonies. COS cells were transfected with the individual plasmid DNA preparations and immunostained with mAb 50-6 in order to identify the clone encoding the antigen recognized by the antibody. A positive clone was identified and the insert was sequenced (FIG. 1A). The open reading frame (SEQ ID NO: 1) of this clone encodes a core protein (FIG. 1B, SEQ ID NO: 2) having a predicted molecular mass of 27.8 kD. There are four distinct hydrophobic domains, and a single N-glycosylation site in a large hydrophilic region that separates the third and fourth hydrophobic domains. Comparison of the sequence of this clone with the NCBI database identified the metastasis-associated antigen as PETA-3/CD151, a recently described member of the transmembrane 4 superfamily (TM4SF) of proteins, which are also known as tetraspanins. The coding sequence was identical to that reported by Fitter, et al. (*Blood* 8: 1348–1355, 1995).

Figure 2B:
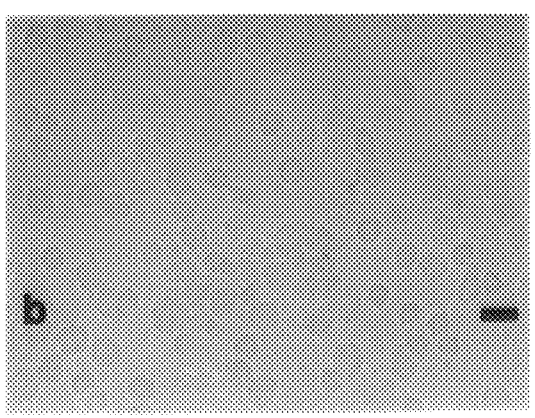
Figure 2C:
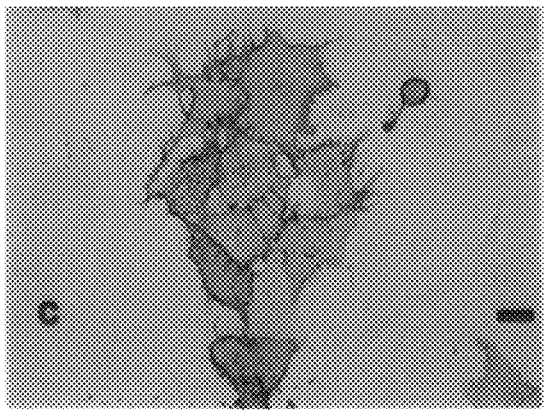
Figure 2D:
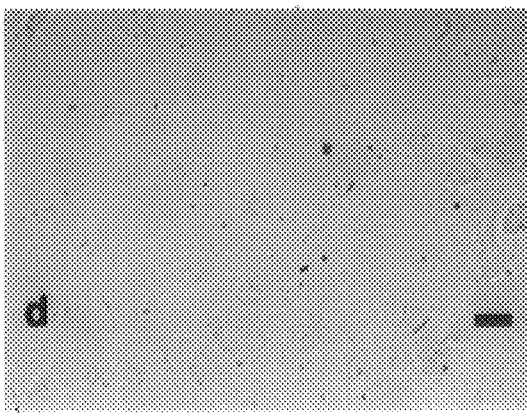
Figure 2E:
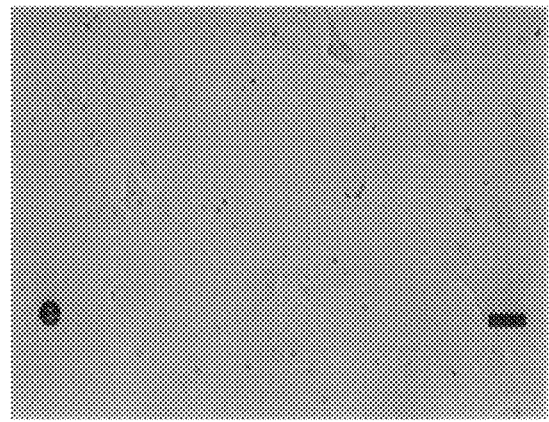

The cell surface distribution of PETA-3 on HEp-3 cells and COS cells transfected with the cloned cDNA was analyzed by immunocytochemistry. On HEp-3 cells incubated with mAb 50-6, there was a strong staining pattern over the entire surface of the cell membrane, including filopods extending from the cell body (FIG. 2a). The same cell surface staining pattern was seen on COS cells transiently transfected with PETA-3 cDNA (FIG. 2c). No signal was observed on HEp-3 or PETA-3-transfected COS cells incubated with normal mouse IgG (FIGS. 2b and 2d), or on control COS transfectants incubated with mAb 50-6 (FIG. 2e).

Figure 3A:
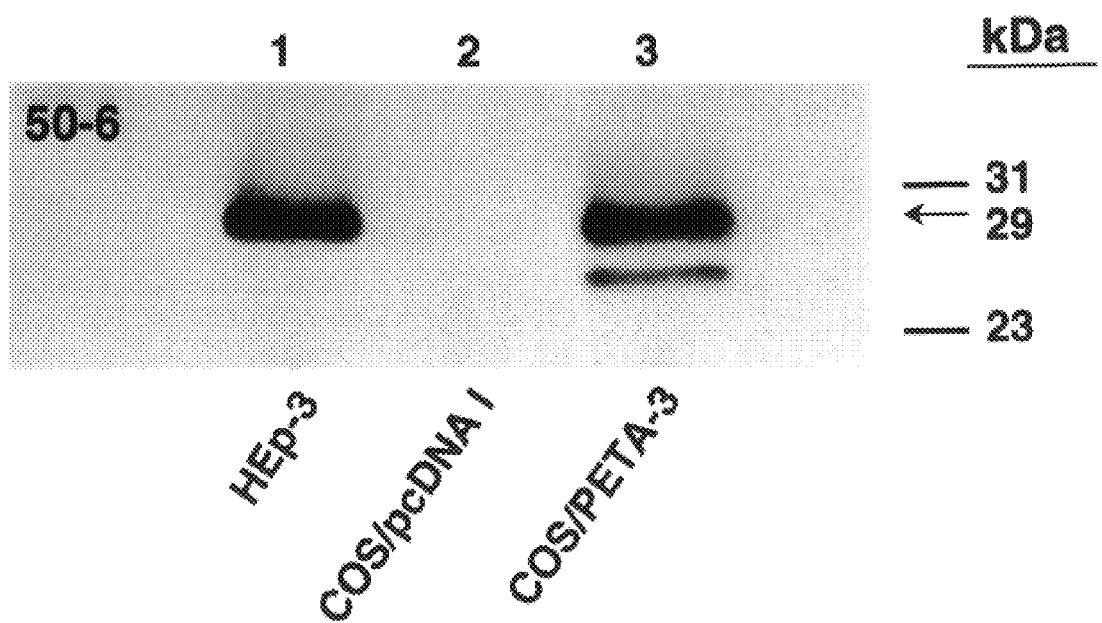
FIGS. 3A–3B depict the recognition of PETA-3/CD151 by mAb 50-6 and mAb 1A5. COS-7 cells were transiently transfected with the cloned PETA-3/CD151 cDNA, or vector (pcDNA I) alone. Lysates of HEp-3 cells and the transfected COS cells were resolved on SDS-PAGE, and analyzed by Western blotting.
Figure 3B:
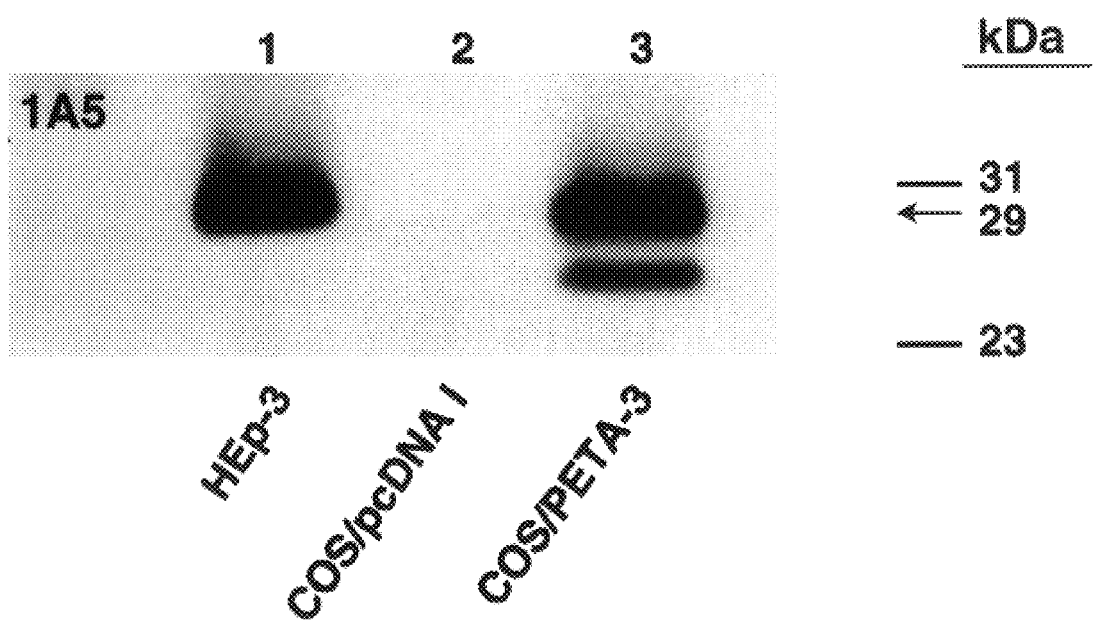

Lysates of HEp-3 cells and PETA-3-transfected COS cells were analyzed by Western Blot using mAbs 50-6 and 1A5. As shown in FIG. 3A, the PETA-3-encoded protein co-migrates with the 29 kD antigen expressed on HEp-3 cells. As shown in FIGS. 3B, mAb 1A5 recognized PETA-3/CD151 expressed by the COS cells (lane 3), whereas no signal was observed in lysates from control transfectants (lane 2). A minor 25 kDa band, immunostained with mAbs 50-6 and 1A5, was also evident in lysates of transfected COS cells (FIGS. 3A and 3B) and in HEp-3 lysates (visible upon prolonged exposure of the Western blot). This 25 kDa band is likely the non-glycosylated form of the protein, since cultivation of HEp-3 cells with tunicamycin or treatment of HEp-3 cell lysates with N-glycanase generates a 25 kDa band that is immunoreactive with mAb 1A5.

These results demonstrate that both mAb 50-6 and mAb 1A5 recognize PETA-3.

EXAMPLE 4

Expression of the Target Antigens

Expression of the Target Antigen of mAb 41-2

Figure 4:
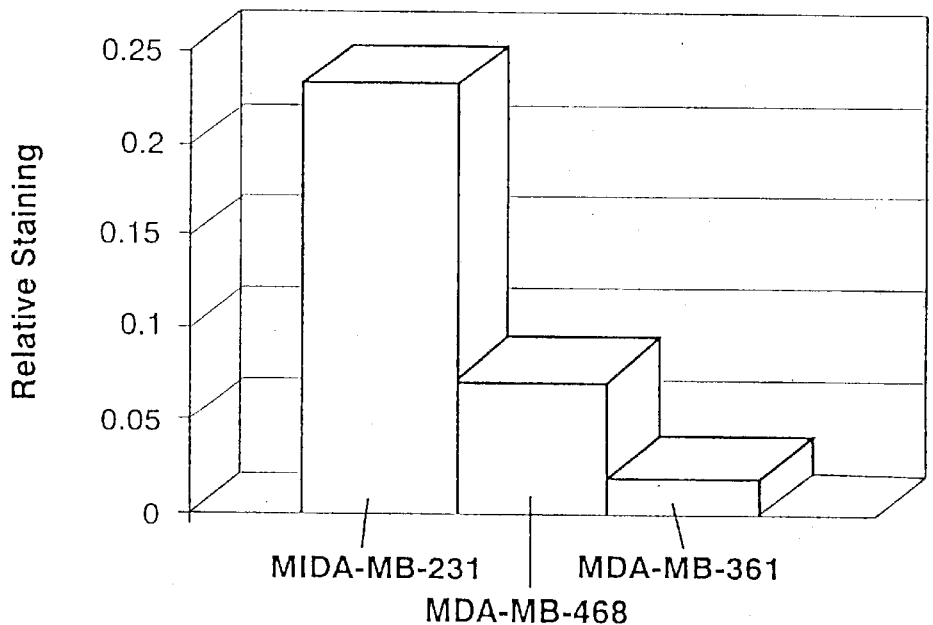
FIG. 4 depicts the relative immunostaining of human breast carcinoma cell lines with mAb 41-2.

Cell lines were examined for expression of the target antigen of mAb 41-2 by whole cell ELISA as described in Example 1. Positive staining by mAb 41-2 was observed with human epidermoid carcinoma HEp-3 cells as well as several human breast carcinoma cell lines. Among the human breast carcinoma cell lines examined (FIG. 4), MDA-MB-231 cells showed the highest immunoreactivity; immunostaining of the MDA-MB-468 cells was about 32% that of the MDA-MB-231 cells; and there was little reactivity with MDA-MB-361 cells (about 6% of that seen with MDA-MB-231). The metastatic potential of these three breast carcinoma cells lines has been quantitated and ranked by Zhang et al. (*Invasion and Metastasis* 11: 204–215, 1991) as follows: MDA-MB-231>MDA-MB-468>MDA-MB-361, from highest to lowest. Thus the immunoreactivity of these cells with mAb 41-2 correlated with their relative metastatic potential.

Figure 5:
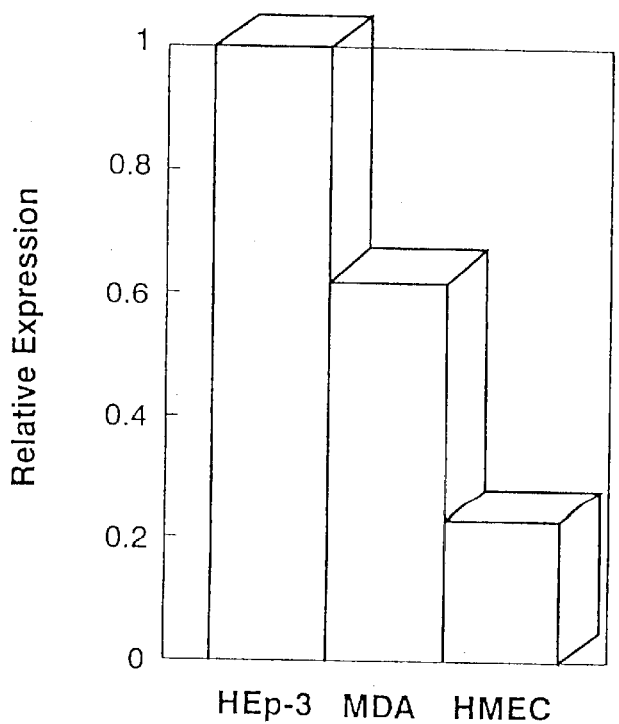
FIG. 5 depicts the relative expression of the antigen recognized by mAb 41-2 in whole-cell ELISA of HEp-3, MDA-MB-231, and normal human mammary epithelial cells (HMEC).

The expression of the target antigen of mAb 41-2 in normal human mammary epithelial cells or HMEC (primary cell cultures from Clonetics Corp., San Diego, Calif.) was compared with the expression in MDA-MB-231 cells or HEp-3 cells in a Whole Cell ELISA assay. As shown in FIG. 5, the level of expression of the target antigen in HMEC was 2.7-fold lower than that in the metastatic human breast carcinoma cell line MDA-MB-231.

Figure 6:
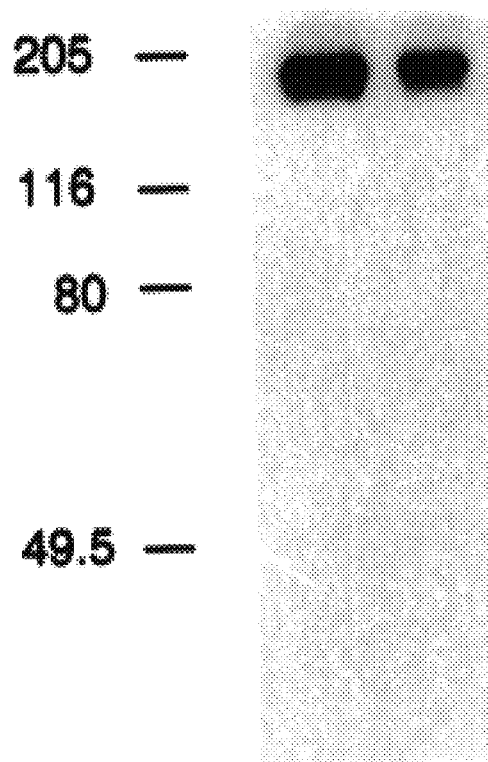
FIG. 6 depicts the western blot analysis of HEp-3 and MDA-MB-231 lysates with mAb 41-2.

The antigen expressed by MDA-MB-231 cells comigrates with the HEp-3 antigen on Western Blots (FIG. 6).

Expression of the Target Antigen of mAb 50-6

Figure 7:
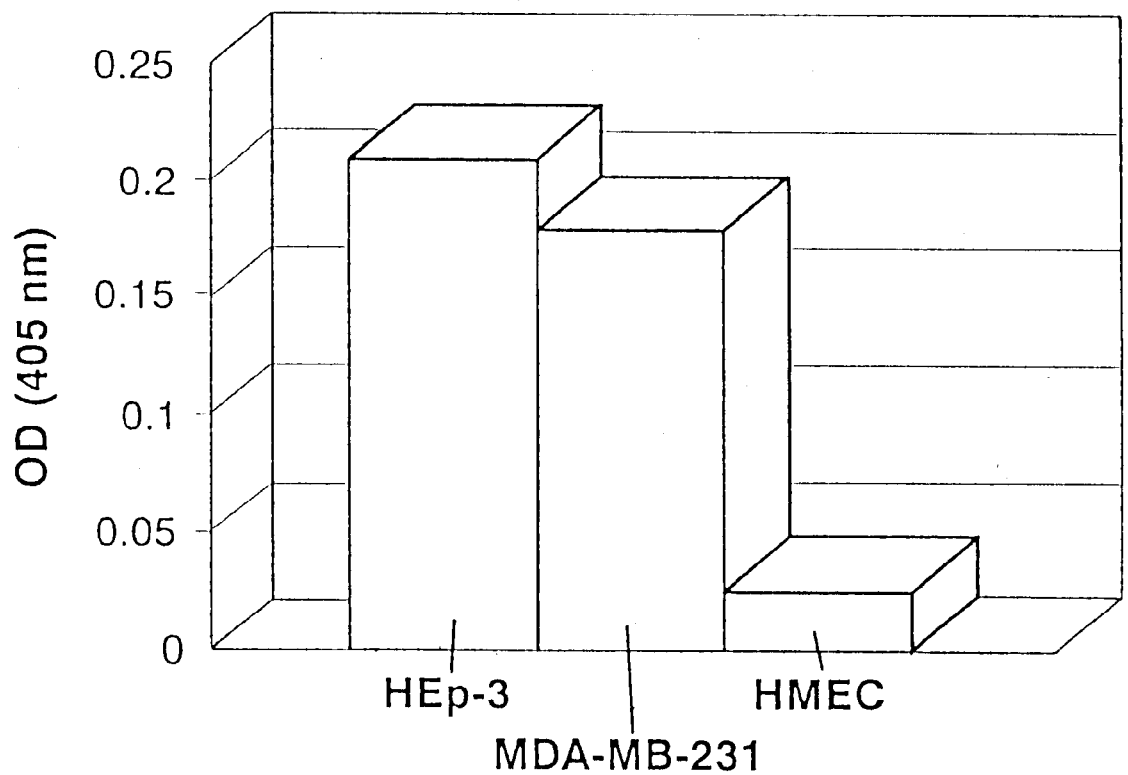
FIG. 7 depicts whole cell ELISA of cell-surface PETA-3 expression by equal numbers ($2 \times 10^4$) of HEp-3 cells, MDA-MB-231 human breast carcinoma cells, and normal human mammary epithelial cells (HMEC; Clonetics). Background signals from normal mouse IgG controls have been subtracted from the data shown.

PETA-3 was found to be expressed by HeLa cells, HT1080 cells (human fibrosarcoma line), M24met cells (human melanoma line), and MDA-MB-231 cells (human breast carcinoma cell line). In addition, when compared to normal human mammary epithelial cells, the level of PETA-3 expression by the MDA-MB-231 cells is ten times higher (FIG. 7).

EXAMPLE 5

Inhibition of Tumor Cell Metastasis by mAb 41-2, mAb 50-6 and mAb 1A5

The effects of the mAbs on tumor metastasis were examined using human epidermoid carcinoma HEp-3 cells in a chick embryo metastasis assay system. Both spontaneous metastasis and experimental metastasis were analyzed.

Spontaneous Metastasis Assays

A small window was cut through the shell with the use of a small model grinding wheel (Dremel, Division of Emerson Electric Co., Racine, Wis.). HEp-3 cells ($2 \times 10^5$ in 25 µl) were inoculated through the window onto the surface of the underlying chorioallantoic membranes (CAMs) of 10-day old chick embryos. The windows were sealed with sterile tape, and the embryos were returned to the incubator. After 24 hours, a second window was cut in the side of the eggshell directly over a prominent blood vessel, which was located by candling the egg. The shell membrane was made transparent with a drop of paraffin oil and the purified mAb (200 µg per embryo in 100 µl of PBS) was inoculated into the vessel using a 1 cc syringe fitted with a 30 ga needle. Control embryos received the same amount of normal mouse IgG. The second window was sealed and the embryos were incubated for another 6 days. The eggs were then opened and the CAM tumors were excised and weighed as a measure of tumorigenesis. The lungs of the chick embryos were also removed, finely minced and passaged onto the CAMs of a second group of embryos. These embryos were incubated for additional seven days to allow any HEp-3 cells in the lungs to multiply. The "lung tumors" arising from the transferred lungs were then excised, finely minced and the number of HEp-3 cells were identified using a phase contrast microscope. Five randomly selected microscopic fields were counted and the number of HEp-3 cells were recorded. The lung tumors were also assayed biochemically for HEp-3 cells by quantitating human uPA activity.

Human uPA activity was measured in the following manner. Lung tumor minces were placed on ice, homogenized with a tissue grinder (Biospec Products, Bontlesville, Okla.) in 0.9 ml of extraction buffer (25 mM Tris, 0.5% TX-100, pH 8.1), and insoluble material was removed by centrifugation at 10,000 g for 10 min. The concentrations of protein in the lung tumor extracts were determined by the BCA method (Pierce). Lung tumor extracts at a protein concentration of 0.1 mg/ml were assayed for human uPA activity. The uPA assays were performed as described by Friberger (*Haemostasis* 7: 138–145, 1975) in 96 well flat bottom ELISA plates (NUNC, Roskilde, Denmark). Lung tumor extracts (10 µl of the 0.1 mg/ml) were incubated with purified human plasminogen (3 µg/well) for 2 h at 37° C. The S2251 chromogenic substrate (Kabi Vitrum, Stockholm, Sweden) was added (15 µg/3 µl extraction buffer) to each well and the ELISA plates were incubated at 37° C. for 0, 15, 30, 60 and 90 min. The absorbance at 405 nm was read at each time point with a multiscan plate reader. The human uPA activity was calculated by comparison of the sample values with a standard curve derived from human urokinase standards (Leo Pharmaceutical Products, Denmark). uPA activity was calculated as milli units of human uPA activity per mg of lung protein.

Measurement of human uPA and visual scoring provided simple, reproducible and quantitative tests for the metastatic spread of HEp-3 cells in the chick embryo. It was found that MAb 41-2 inhibited spontaneous HEp-3 metastasis by about 63.7% (Table I), MAb 50-6 inhibited spontaneous HEp-3 metastasis by about 74% (Table II), and 1A5 inhibited spontaneous HEp-3 metastasis by about 93%.

Experimental Metastasis Assay

A prominent blood vessel was located in the CAM of 11-day old chicken embryos. A window was cut into the shell over the vessel and the underlying shell membrane was made transparent with a drop of paraffin oil. The tumor cell suspension ($2 \times 10^5$/ml) was incubated with the mAb (2 mg/ml) for 5 minutes at room temperature, then 100 µl of the cell/antibody suspension was inoculated directly into the circulatory system using a 1 cc syringe fitted with a 30 ga needle. Control embryos were inoculated with tumor cells pre-incubated with normal mouse IgG. The window was sealed with a piece of sterile tape and the embryos were incubated for additional 6 days. The assay was then completed as described above for spontaneous metastasis assays.

The results showed that mAb 41-2 inhibited experimental metastasis by about 90.8% (Table I), mAb 50-6 inhibited experimental metastasis by about 56.8% (Table II) and mAb 1A5 inhibited experimental metastasis by about 81%.

TABLE I

Inhibition of HEp-3 metastasis by mAb 41-2.

Spontaneous metastasis

| anitbody | number of embryos | primary tumor wt.* (mean ± SEM) | Lung metastasis+ (huPA in lung) (mean ± SEM) | % inhib |
|---|---|---|---|---|
| NM IgG | 9 | 222 ± 26.2 | 4287 ± 1078 | 0 |
| mAb 41-2 | 11 | 203 ± 23.3 | 1556 ± 437 | 63.70% |

Experimental metastasis

| anitbody | number of embryos | Lung metastasis++ (huPA in lung) (mean ± SEM) | % inhib |
|---|---|---|---|
| NM IgG | 10 | 3855 ± 1025 | 0 |
| mAb 41-2 | 11 | 333 ± 132 | 90.80% |

*P = 0.300; +P = 0.019; ++P = 0.003

TABLE II

Inhibition of HEp-3 metastasis by mAb 50-6.

Spontaneous metastasis

| anitbody | number of embryos | primary tumor wt.* (mean ± SEM) | Lung metastasis+ (huPA in lung) (mean ± SEM) | % inhib |
|---|---|---|---|---|
| NM IgG | 11 | 274 ± 51 | 1015 ± 249 | 0 |
| mAb 50-6 | 13 | 253 ± 46 | 261 ± 117 | 74.30% |

Experimental metastasis

| anitbody | number of embryos | Lung metastasis++ (huPA in lung) (mean ± SEM) | % inhib |
|---|---|---|---|
| NM IgG | 11 | 2169 ± 601 | 0 |
| mAb 50-6 | 10 | 937 ± 299 | 56.80% |

*P = 0.689; +P = 0.022; ++P = 0.044

PETA-3/CD151 mediates an early event in the formation of metastatic foci.

The anti-metastatic properties of mAb 50-6 was not due to a cytostatic or cytotoxic effect of the antibody, since it was found that the antibody had no effect on proliferation of HEp-3 cells in vitro, nor on the size of the primary tumor on the CAM (Table II).

A time-course study of inhibition of experimental metastasis was carried out. The antibodies were inoculated at different times before or after inoculation of the tumor cells. The inoculated embryos were incubated for an additional six days, after which the lungs were excised, finely minced and transferred to prepared CAMs of a second set of embryos. The assay was then completed as described above. As shown in Table III, HEp-3 dissemination to the embryonic lungs was markedly inhibited when mAb 1A5 was administered as early as two hours before or as late as six hours after inoculation of the tumor cells. In contrast, there was little effect on HEp-3 colonization of the lungs when mAb 1A5 was administered 10 or 20 hours after the tumor cells were inoculated. The inability of mAb 1A5 to inhibit lung colonization at the latter time points (when tumor cells would likely have extravasated already) indicates that the antibody did not block metastasis by inhibiting cell growth at the secondary sites.

These experiments indicate that PETA-3/CD151 mediated HEp-3 dissemination by affecting an earlier event such as cell adhesion to the vessel wall, extravasation, and/or tumor cell migration to selective sites of secondary growth.

TABLE III

Time Course or inhibition of HEp-3 experimental metastasis.

| antibody | time of Ab inoculation | number of embryos | Lung metastasis (huPA in lung) (mean ± SEM) | % inhib |
|---|---|---|---|---|
| NM IgG | −2 hr | 47 | 1522 ± 54 | 0 |
| mAb 1A-5 | −2 hr | 36 | 295 ± 60 | 81 |
| mAb 1A-5 | +6 hr | 21 | 401 ± 36 | 74 |
| mAb 1A-5 | +10 hr | 8 | 1471 ± 36 | 3 |
| mAb 1A-5 | +20 hr | 20 | 1408 ± 67 | 7 |

EXAMPLE 6

Inhibition of Tumor Cell Invasion by mAb 41-2

Figure 8:
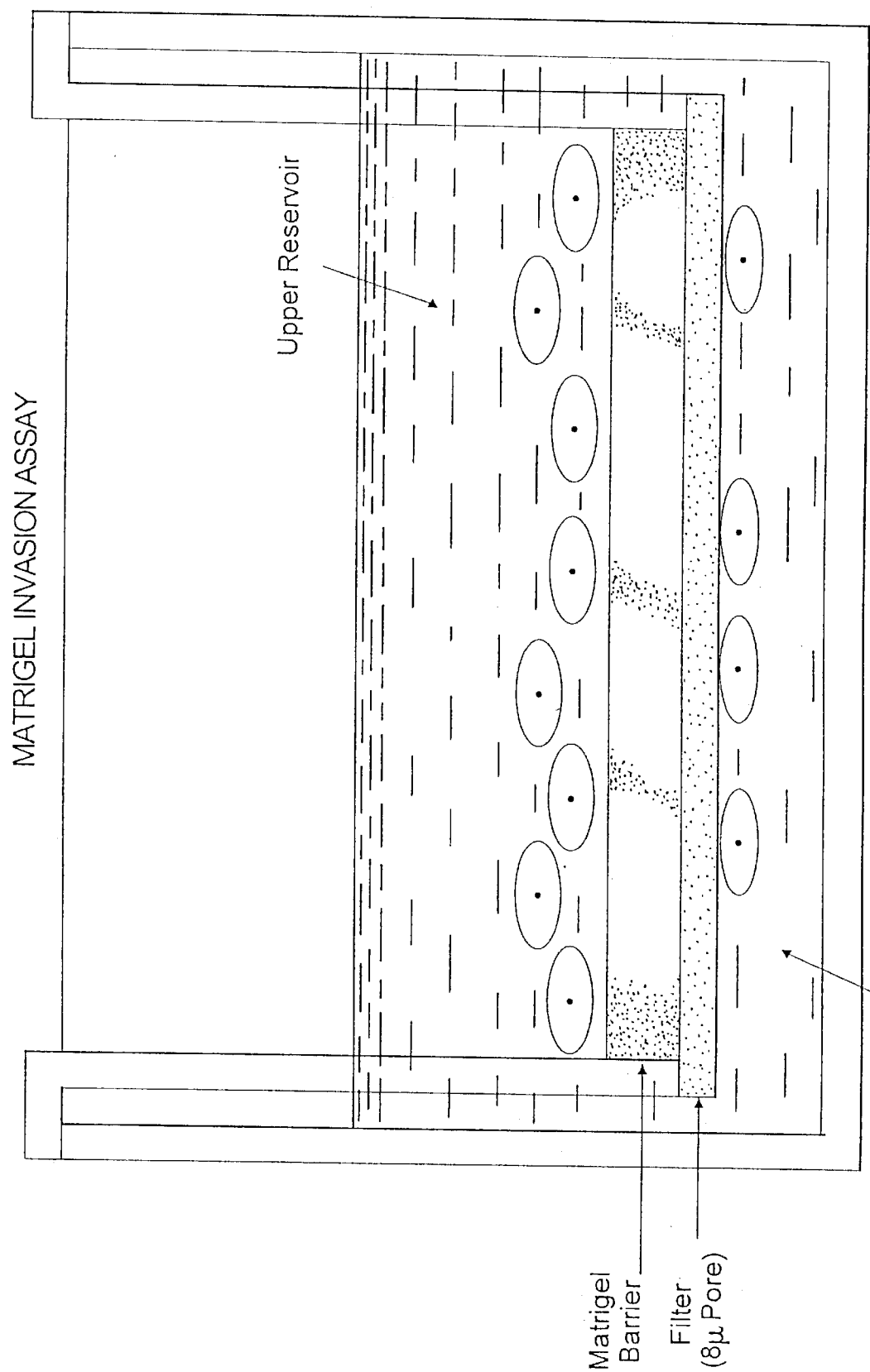
FIG. 8 graphically depicts a Matrigel invasion assay.

Matrigel-coated invasion chambers (Biocoat Invasion Chambers, 24-well format) were purchased from Collaborative Research Products and prepared (rehydrated) according to the manufacturer's instructions. Tumor cell suspensions were prepared with Non-enzymatic Cell Dissociation Solution (Sigma). MAb (50 µg/ml) was included in the upper chamber with the tumor cells ($1 \times 10^4$/well) and in the lower reservoir which contained NIH-3T3 conditioned medium as a chemoattractant. Control chambers received normal mouse IgG (50 µg/ml). The chambers were incubated at 37° C. in 5% $CO_2$ and, after 70 hr, the cells on the upper surface of the filters were removed by wiping with a cotton swab. The filters were then fixed with methanol and stained with hematoxylin and eosin, and the number of cells per microscopic field were counted from the underside of the filter. FIG. 8 graphically depicts such invasion assay.

Figure 9A:
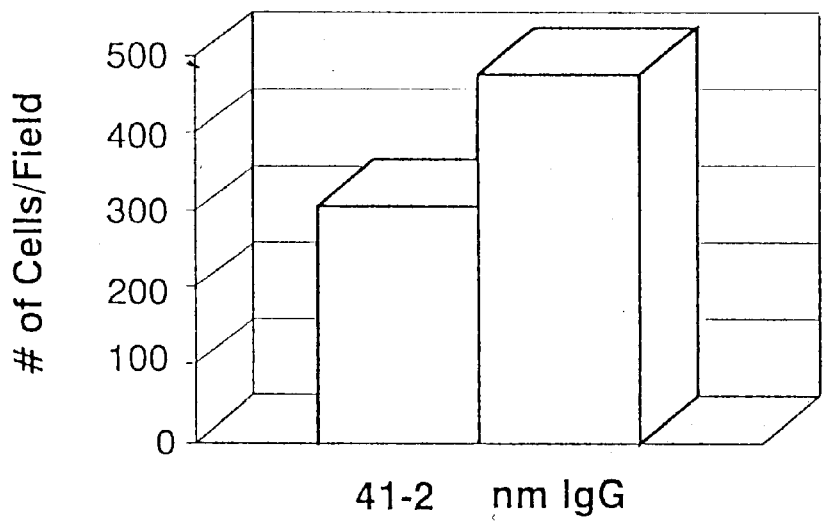
FIGS. 9A–9B depict the inhibition of Matrigel invasion by mAb 41-2. MDA-MB-231 cells and HEp-3 cells were placed in Matrigel invasion chambers (Collaborative Research) in the presence of mAb 41-2 or normal mouse IgG. Data are expressed as the number of cells on the underside of the filter (i.e., invasive cells) per microscopic field.
Figure 9B:
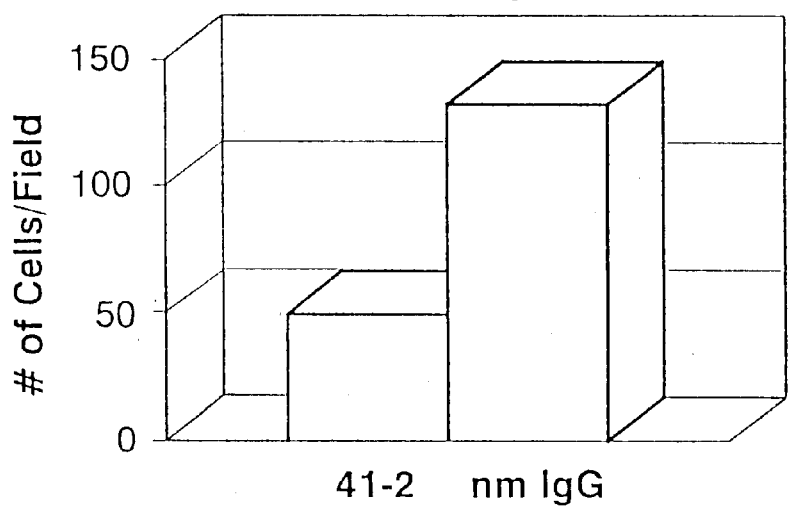

As shown in FIGS. 9A–9B, mAb 41-2 inhibited Matrigel invasion by both HEp-3 cells and MDA-MB-231 cells. MAb 41-2 inhibited invasion of MDA-MB-231 cells by 38%, and inhibited invasion of HEp-3 invasion by 63%, when compared to the control chambers. Under identical conditions, mAb 41-2 had no effect on invasion by HT1080, a human fibrosarcoma cell line (American Type Culture Collection, 12301 Parklawn Drive, Rockville, Md., 20852-1776) which was not recognized by this antibody.

EXAMPLE 7

Inhibition of Tumor Cell Migration by mAb 41-2, mAb 50-6 and mAb 1A5

Figure 10:
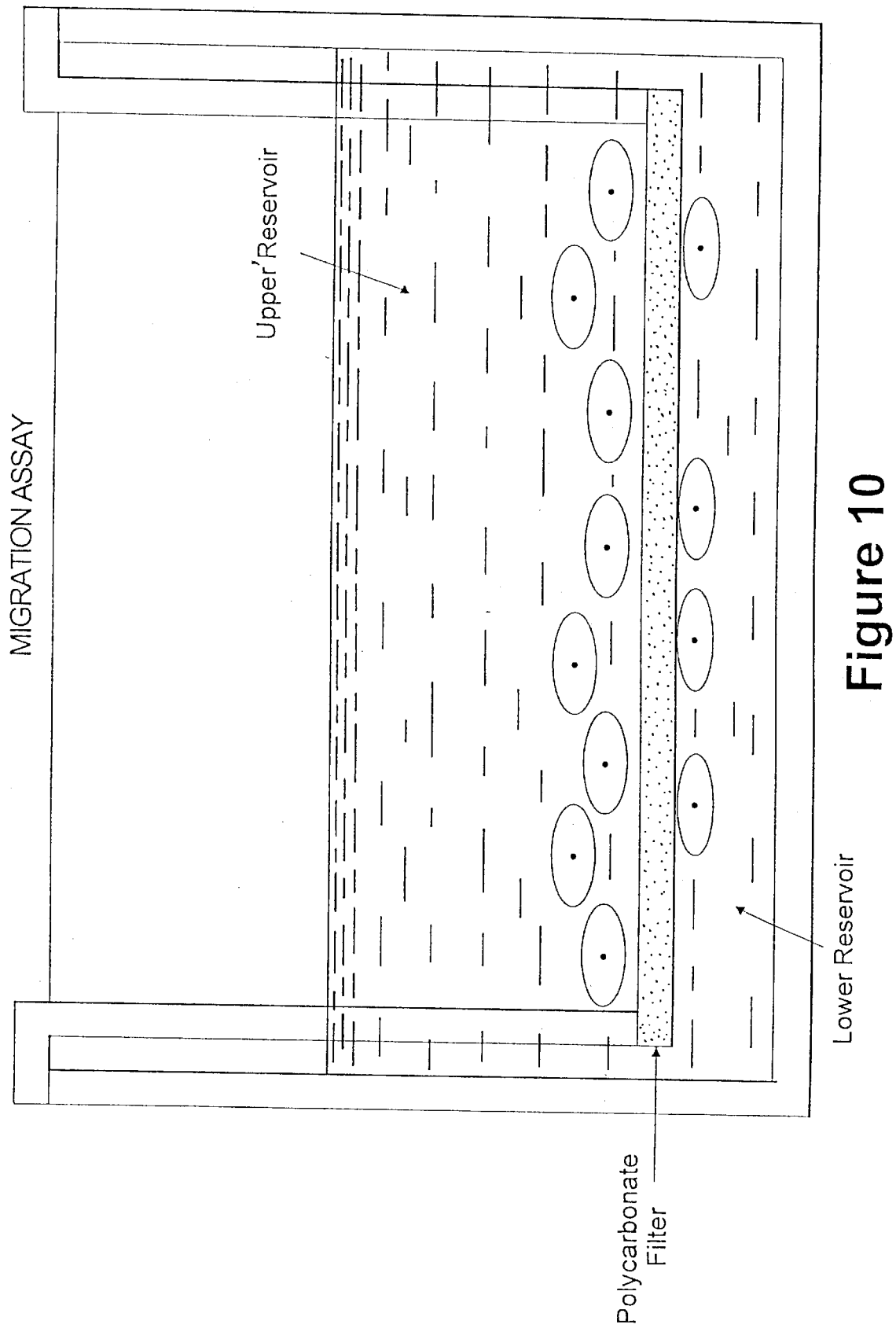
FIG. 10 graphically depicts a cell migration assay.

Control invasion chambers (no coating on the filter, 24-well format) were purchased from Collaborative Research Products. mAb (50 μg/ml), together with the tumor cells ($2 \times 10^4$/well), was added in the upper chamber. mAb (50 μg/ml) was also added in the lower reservoir having serum-containing medium as a chemoattractant. In control chambers, normal mouse IgG (50 μg/ml) was used in place of mAb. The chambers were incubated at 37° C. in 5% $CO_2$. After 18 hr, the cells on the upper surface of the filters were removed by wiping with a cotton swab. The filters were then fixed with methanol and stained with hematoxylin and eosin, and the number of migrated cells per microscopic field was recorded from the underside of the filter. FIG. 10 graphically depicts such migration assay.

Figure 11:
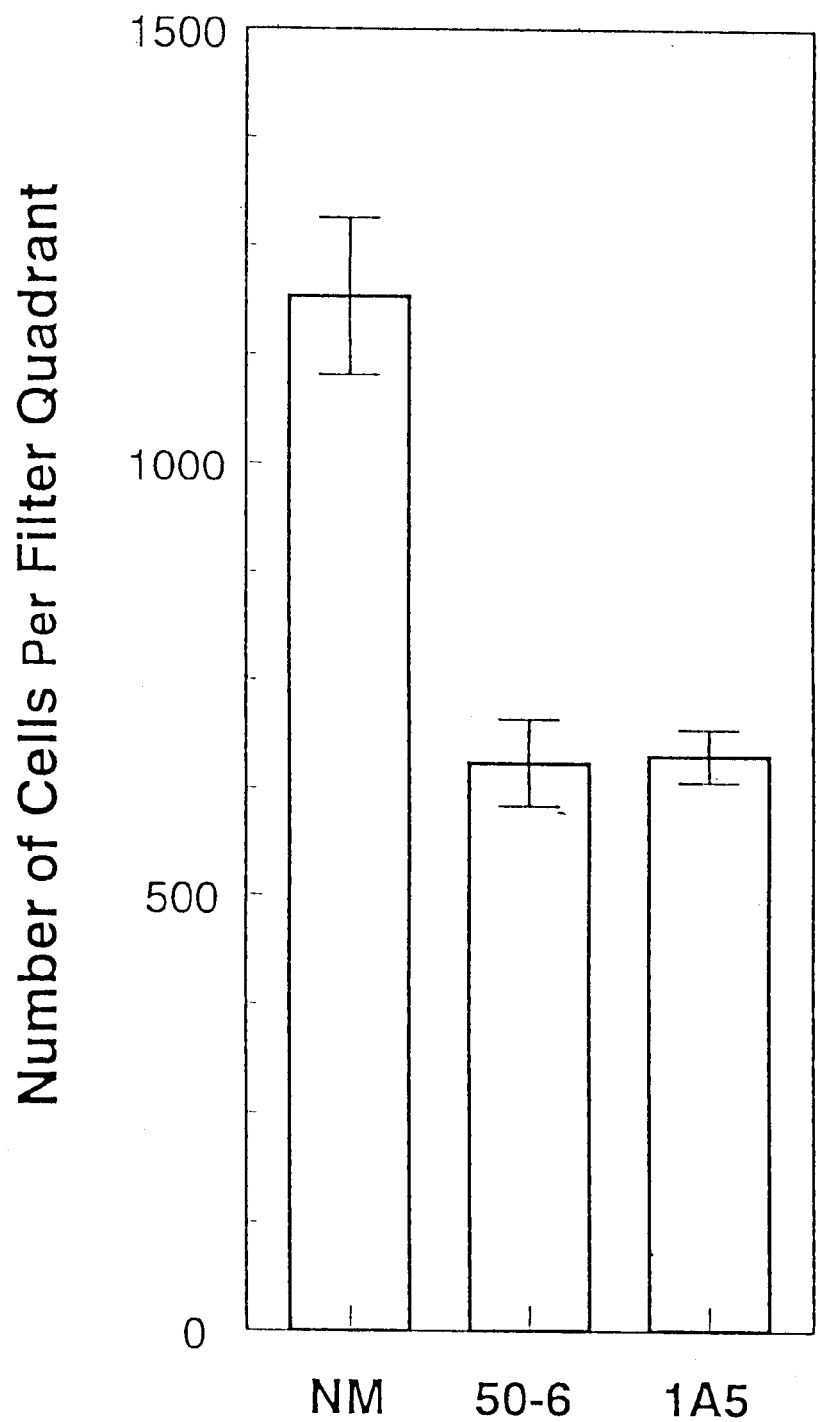
FIG. 11 depicts the inhibition of HEp-3 migration by mAb 50-6 and mAb 1A5. Experiments were conducted in triplicate.

It was found that mAb 41-2 inhibited HEp-3 migration by approximately 50%. mAb 50-6 and mAb 1A5 inhibited HEp-3 migration by approximately 45% and 44%, respectively, when compared to controls (P=0.034) (FIG. 11).

Figure 12C:
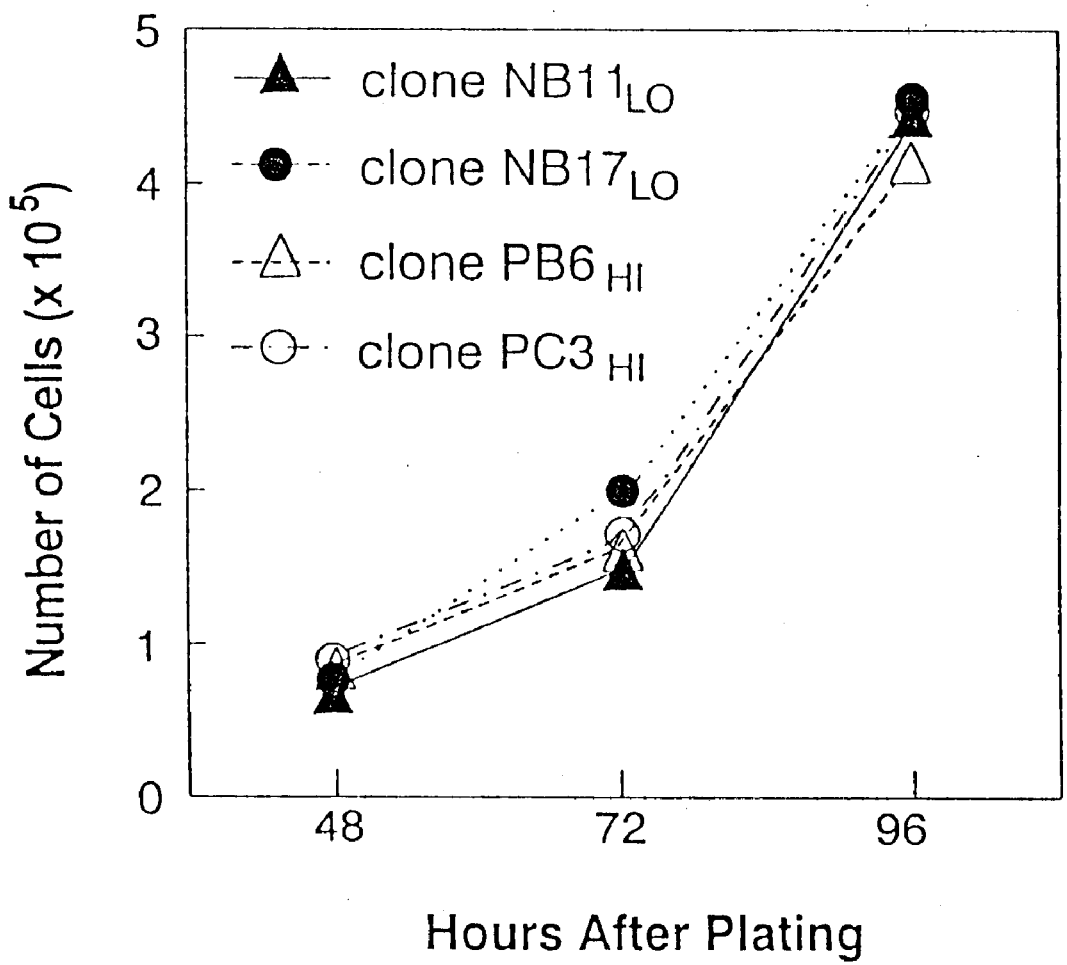
Figure 12E:
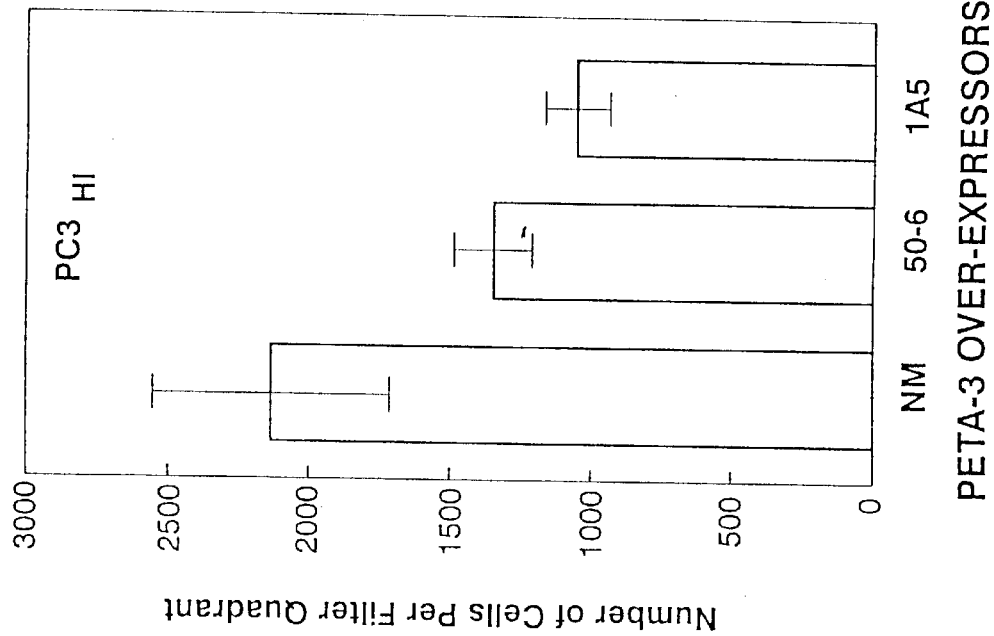
Figure 12D:
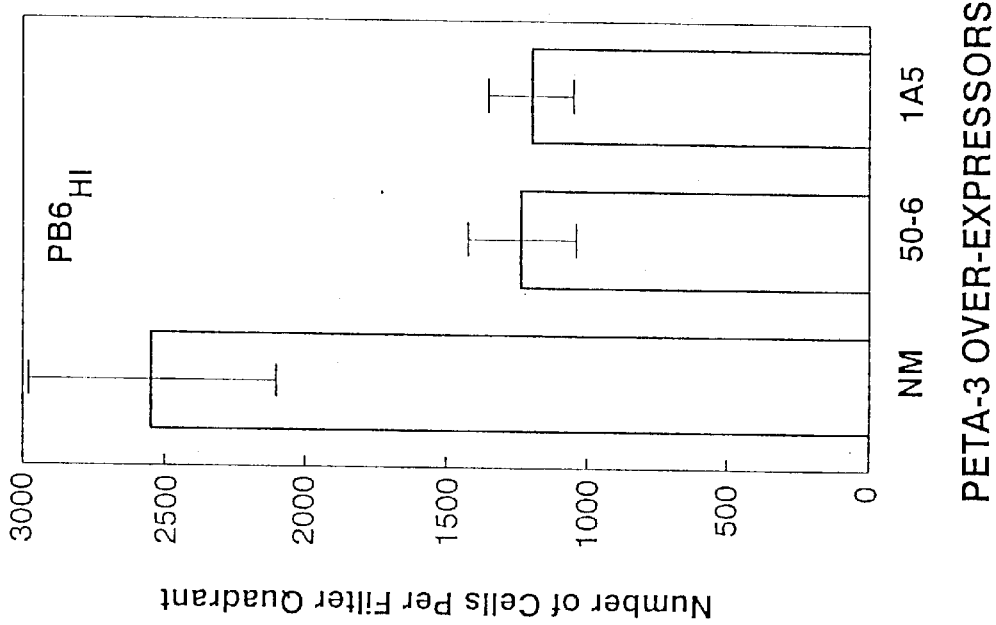
Figure 12G:
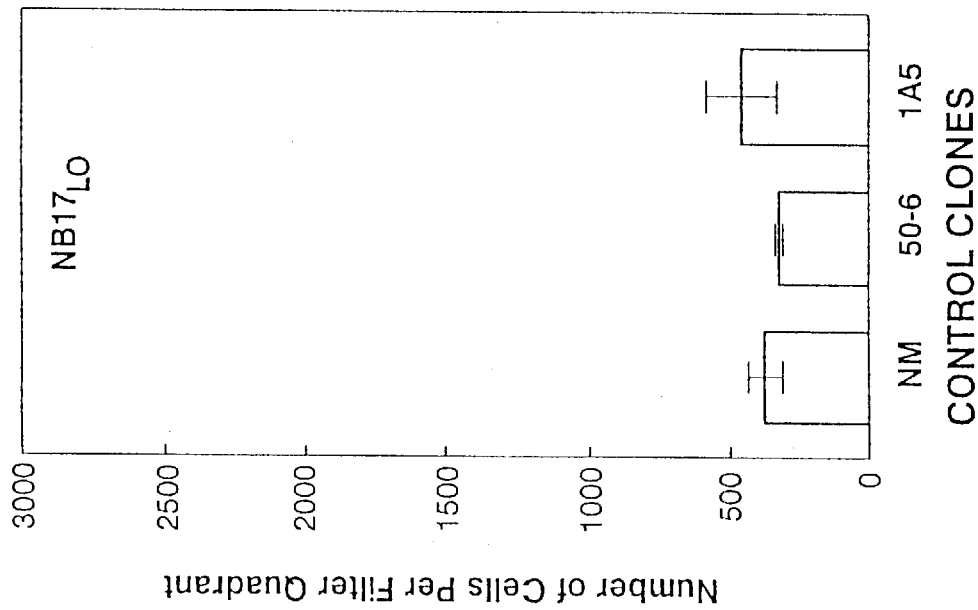
Figure 12F:
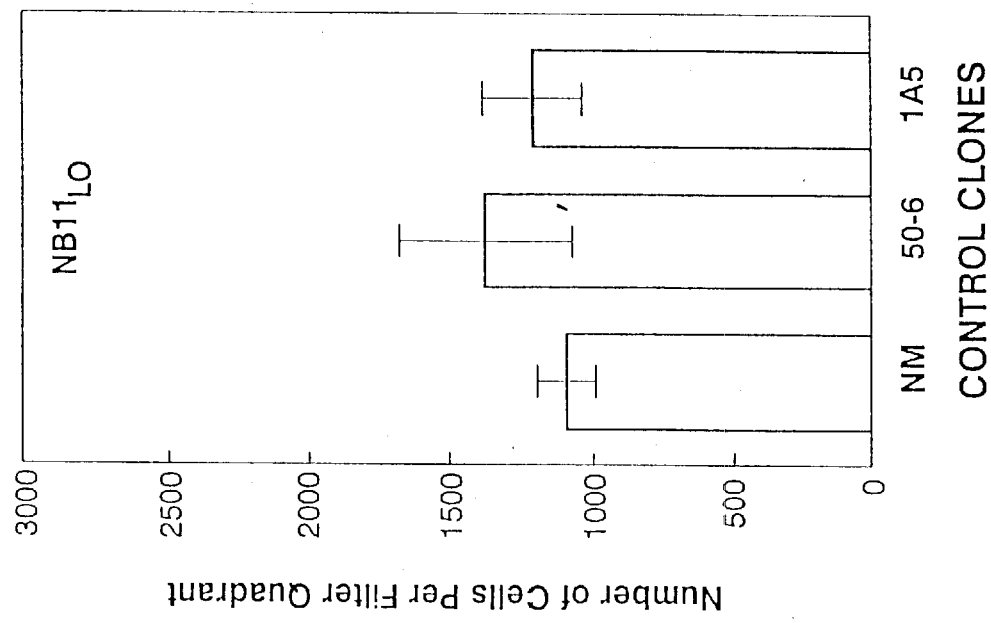

To further demonstrate the role of PETA-3/CD151 in tumor cell migration, HeLa cells were transfected with the cloned cDNA, or with vector alone. Two clones from each group were selected on the basis of the PETA-3 expression levels, the similar rates of growth in vitro and similarity in morphological appearance. The levels of cell-surface PETA-3 on the two over-expressing clones, $PB6_{HI}$ and $PC3_{HI}$ were about two-fold higher than the HEp-3 cells, while the control transfectants, $NB11_{LO}$ and $NB17_{LO}$ expressed approximately one quarter to one half the amount detected on HEp-3 cells (FIGS. 12A–12B). The growth rates of the four clones were identical (FIG. 12C). Migration by the over-expressing clones $PB6_{HI}$ and $PC3_{HI}$ was significantly higher than the underexpressing control transfectants $NB11_{LO}$ and $NB17_{LO}$ (FIGS. 12D–12G; P=0.001). When mAb 50-6 or mAb 1A5 (50 μg/ml) was added to the chambers, migration of clone $PB6_{HI}$ was significantly reduced (P=0.034) by 51.6% and 52.8%, respectively, while migration of clone $PC3_{HI}$ was significantly reduced (P=0.007) by 36.7% and 50.6%, respectively, lowering the motility of these cells to the level of control $NB11_{LO}$ cells. Neither mAb 50-6 nor mAb 1A5 inhibited migration of the weakly expressing clones $NB11_{LO}$ (P=0.729) or $NB17_{LO}$ (P=0.337), indicating that migration by these cells was mediated by a PETA-3-independent mechanism.

EXAMPLE 8

Association of PETA-3 with Integrin $\alpha_3\beta_1$

A monoclonal antibody, mAb 1992, which specifically recognizes the $\alpha_3\beta_1$ heterodimer, was used in whole cell ELISA. The $\alpha_3\beta_1$ integrin was detected on HEp-3 cells (FIG. 13) at levels equivalent to known positive controls, MDA-MB-231, a human breast carcinoma cell line, and HT1080, a human fibrosarcoma cell line.

HEp-3 cell lysates were immunoprecipitated with mAb 1992 as follows. HEp-3 cells were in lysed in Brij lysis buffer (1% Brij 98, 25 mM HEPES, pH 7.5, 150 mM NaCl, 5 mM $MgCl_2$, 10 μM E64, 20 U/ml Aprotinin, 20 μg/ml soybean trypsin inhibitor (all from Sigma)) for one hr with constant rocking at 4° C. Insoluble material was removed by centrifugation at 12,000 g for 5 minutes at 4° C. The lysate was pre-cleared with GammaBind Plus Sepharose beads. Aliquots of the extract representing $10^7$ cells were incubated with either 25 μg of mAb 1A5, 10 μg of mAb 1992 (Chemicon, Temecula, Calif.), or 25 μg of normal mouse IgG (Sigma, St. Louis, Mo.). Fifty μl of packed GammaBind Plus Sepharose beads were added to each sample and the mixtures were incubated at 4° C. overnight with constant rocking. The beads were then washed with the Brij lysis buffer, and the immune complexes were eluted with Laemmli sample buffer at 95° C. for two minutes. The eluted proteins were resolved on a 10% SDS-PAGE gel, transferred to nitrocellulose. Because biotinylation of both mAb 1A5 and mAb 50-6 destroys their immunoreactivity, PETA-3 was detected by incubating the blots with unlabeled mAb 1A5 followed by horseradish peroxidase-conjugated goat anti-mouse IgG.

Figure 14:
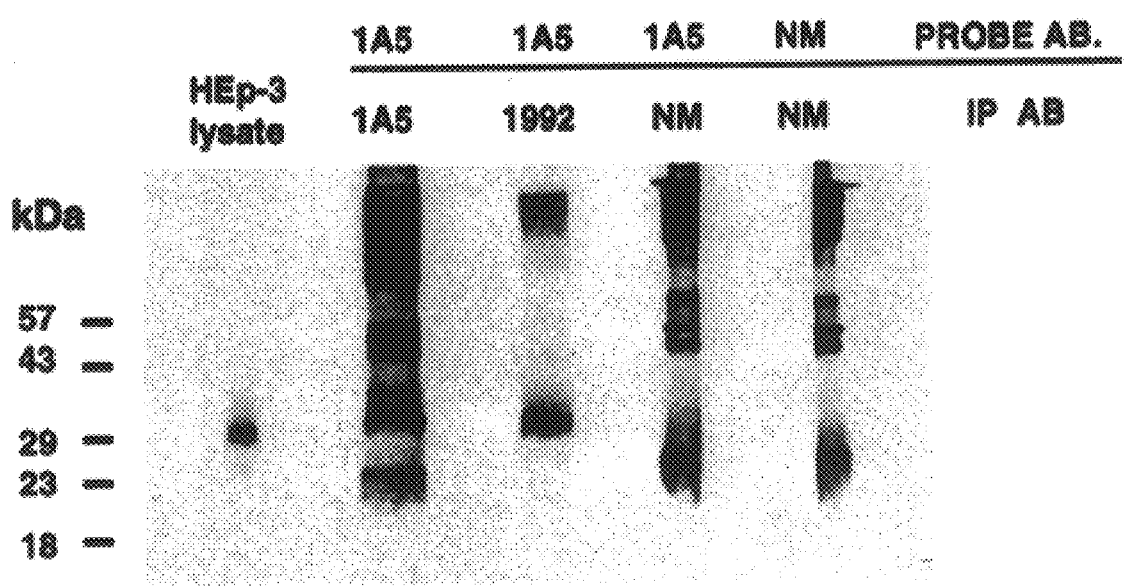
FIG. 14 depicts PETA-3 expressed by HEp-3 cells associates with the $\alpha_3\beta_1$ integrin heterodimer. HEp-3 cell lysates were incubated with mAb 1A5 (lane 2), mAb 1992 (specific for the $\alpha_3\beta_1$ heterodimer; lane 3), or normal mouse IgG (NM; lane 4). Immune complexes were collected on GammaBind Plus Sepharose, resolved by SDS-PAGE and transferred to nitrocellulose. The blot was incubated with unlabeled mAb 1A5 as a primary antibody, followed by horseradish peroxidase-conjugated goat anti-mouse IgG. Signals were visualized by chemiluminescence. As a control, a NM immunoprecipitate was probed with NM IgG and peroxidase-conjugated goat anti-mouse IgG (lane 5). A sample of the original HEp-3 lysate is shown in lane 1. The PETA-3 signal is indicated by *. Molecular weight markers in kilodaltons (kD) are shown to the left.

Western blot analysis of immunoprecipitates obtained with mAb 1992 revealed a 29 kD protein which immunostained with mAb 1A5 (FIG. 14, lane 3). This protein co-migrated with the authentic antigen present in the HEp-3 lysates (FIG. 14, lane 1) and in immunoprecipitates obtained with mAb 1A5 (FIG. 14, lane 2). No PETA-3 signal was observed in control normal mouse IgG immunoprecipitates probed with mAb 1A5 (FIG. 14, lane 4) or normal mouse IgG (FIG. 14, lane 5). The background bands observed in the immunoprecipitated samples are due to the reactivity of the secondary antibody to mouse IgG proteins and IgG fragments as seen in the control lanes.

Figure 13:
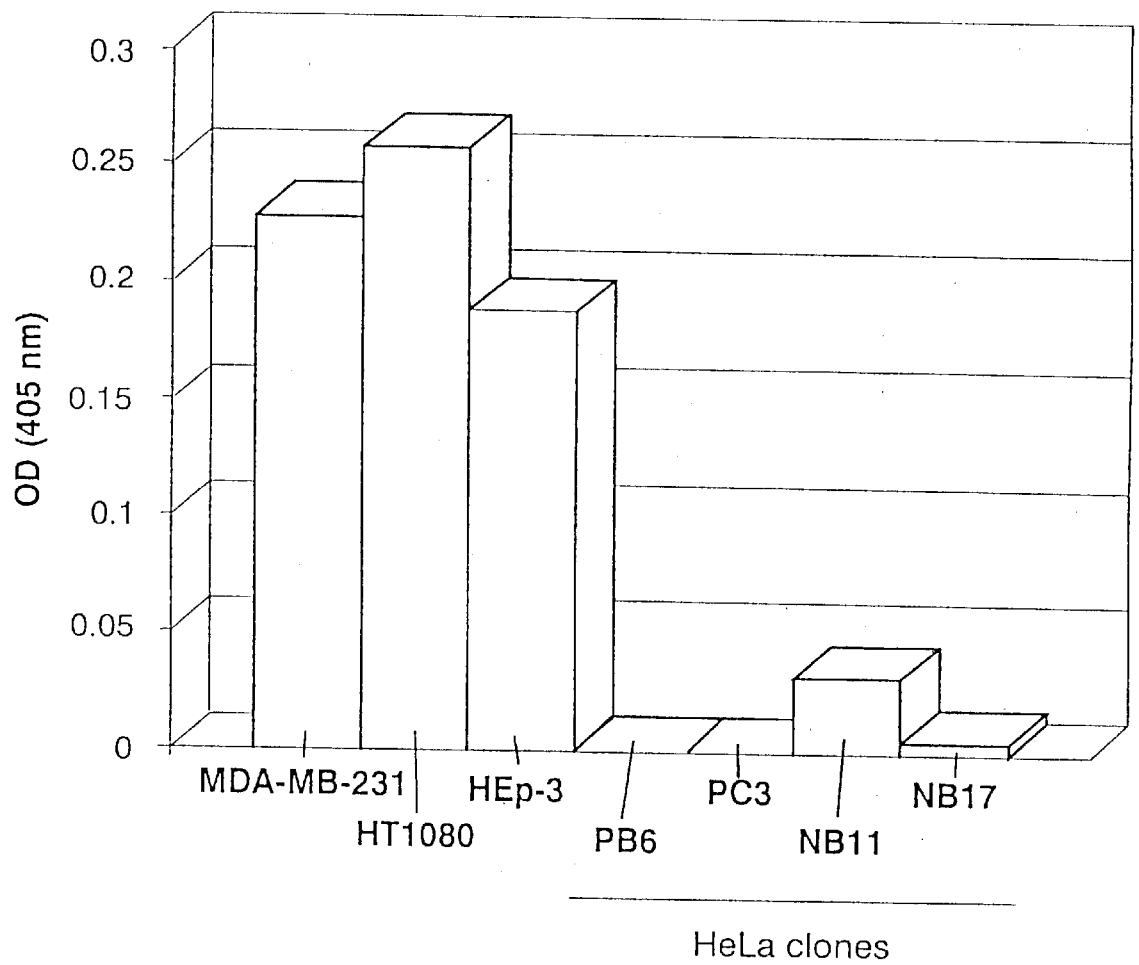
FIG. 13 depicts whole-cell ELISA of expression of the $\alpha_3\beta_1$ integrin heterodimer by equal numbers ($2 \times 10^4$) of MDA-MB-231 human breast carcinoma cells, HT1080 human fibrosarcoma cells, HEp-3 cells, and the PETA-3 overexpressing HeLa clones ($PB6_{HI}$, $PC3_{HI}$) and control HeLa clones ($NB11_{LO}$, $NB17_{LO}$). MAb 1992 was used to specifically identify the heterodimer. Data represent the amount of chromogen released in the assay and are expressed as the optical density (OD) at 405 nm.

When the PETA-3-transfected HeLa clones were analyzed by whole-cell ELISA, there was no detectable $\alpha_3\beta_1$ signal. Weak signals were seen with the control HeLa transfectant (FIG. 13). This indicates that PETA-3 interacts with a different integrin in the transfected HeLa cells to effect the observed increase in cell migration (FIGS. 12D–12G).

EXAMPLE 9

Effects of the Monoclonal Antibodies on Cell Adhesion

HEp-3 cells and the HeLa transfectants were tested for adhesion to various purified matrix proteins in the presence of mAb 50-6, mAb 1A5 or normal mouse IgG. HEp-3 cells, PETA-3-overexpressing HeLa clones ($PB6_{HI}$, $PC3_{HI}$) and control HeLa clones ($NB11_{LO}$, $NB17_{LO}$) were added to the wells of 96-well plates coated with either fibronectin (FN) or vitronectin (VN) in the presence of 50 μg/ml mAb 50-6, mAb 1A5 or normal mouse IgG and incubated for 30 minutes. Non-adherent cells were gently washed away, and the amount of cell adhesion was determined by crystal violet staining. Data are expressed as the optical density (OD) at 595 nm of the incorporated crystal violet dye, and are representative of two separate experiments conducted in triplicate.

Figure 15A:
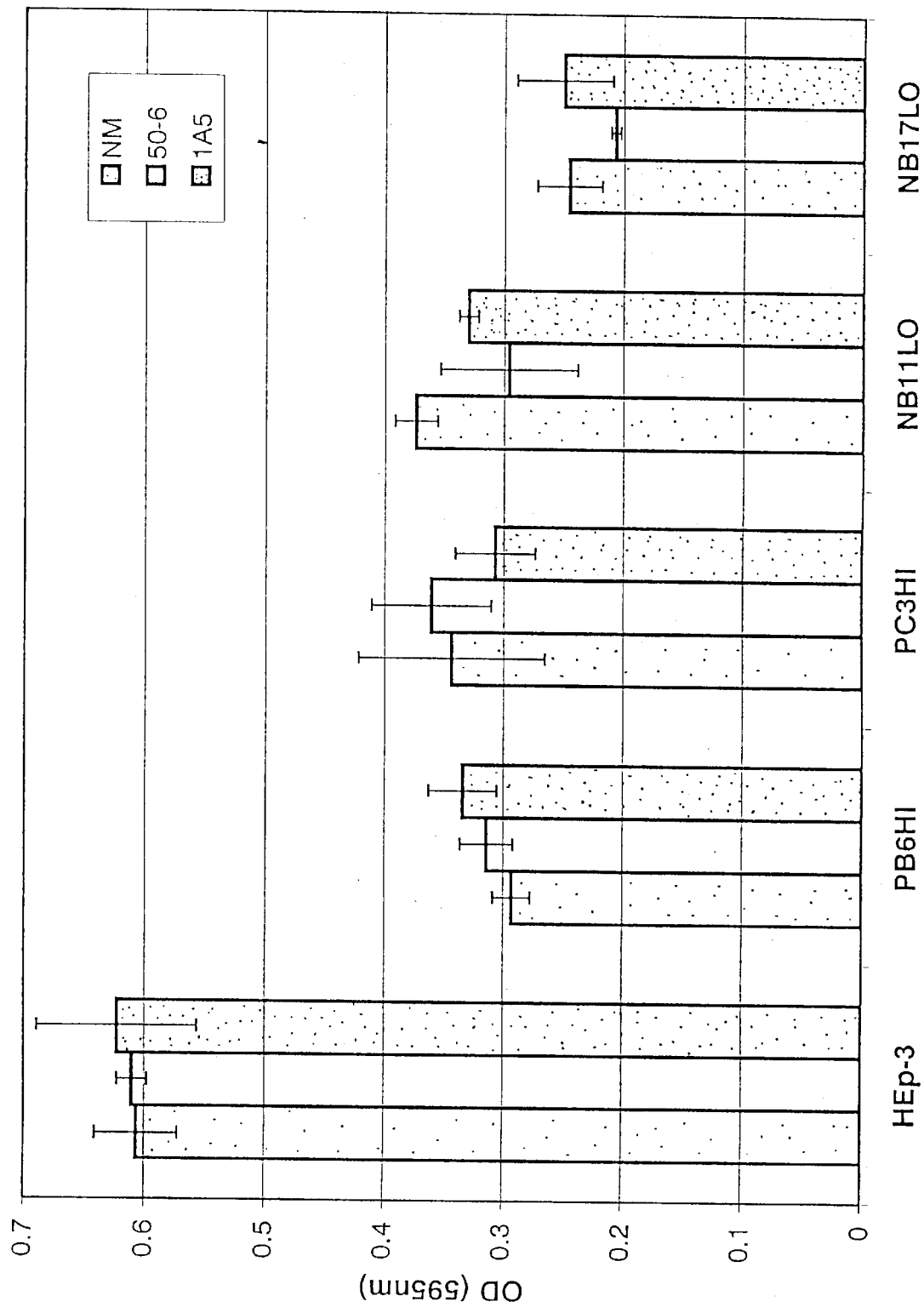
FIG. 15A depicts the effects of mAb 50-6 and mAb 1A5 on cell adhesion to fibronectin of HEp-3 cells, PETA-3-overexpressing HeLa clones ($PB6_{HI}$, $PC3_{HI}$) and control HeLa clones ($NB11_{LO}$, $NB17_{LO}$).
Figure 15B:
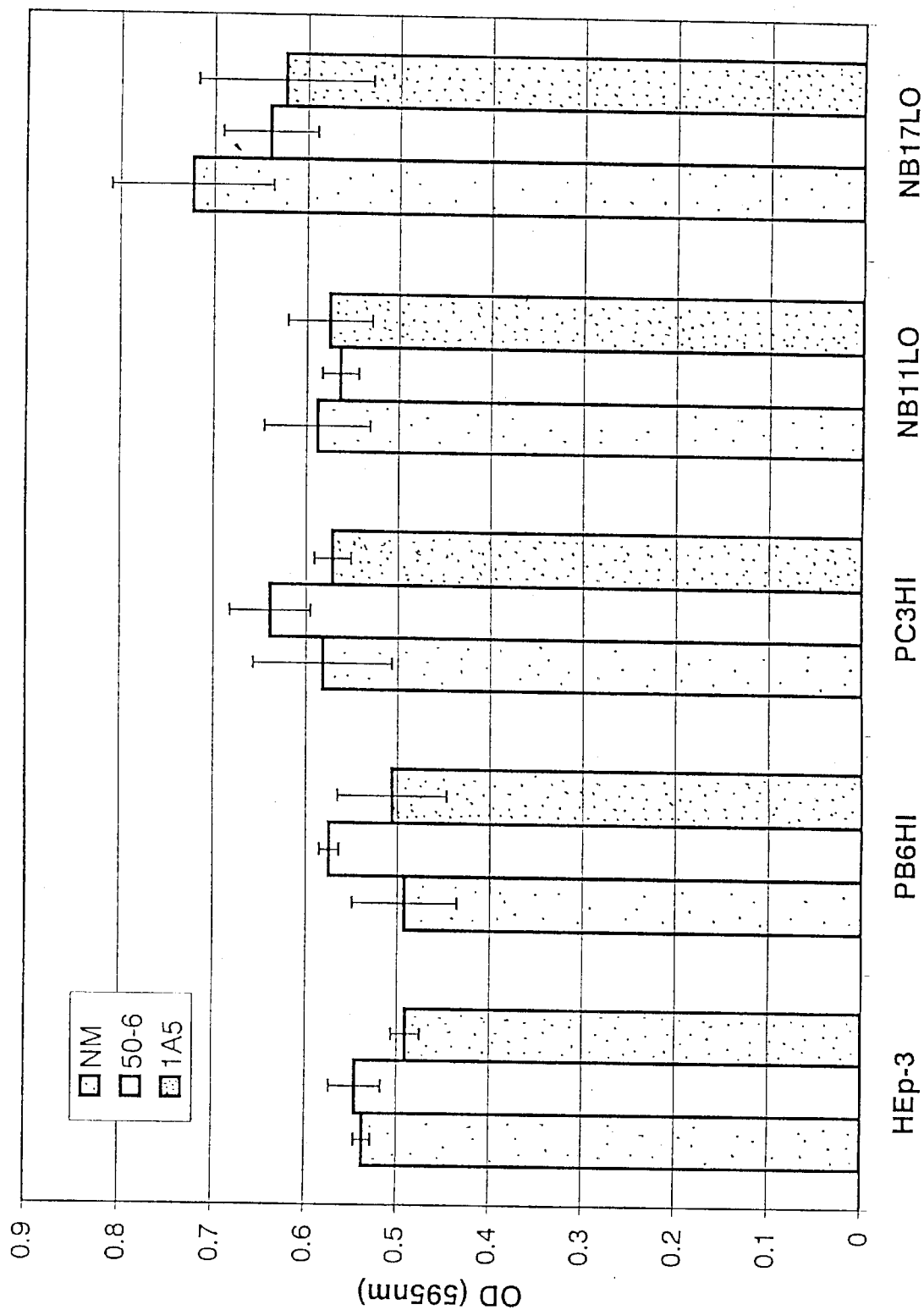
FIG. 15B depicts the effects of mAb 50-6 and mAb 1A5 on cell adhesion to vitronectin of HEp-3 cells, PETA-3-overexpressing HeLa clones ($PB6_{HI}$, $PC3_{HI}$) and control HeLa clones ($NB11_{LO}$, $NB17_{LO}$).

As shown in FIGS. 15A–B, at the 30 minute time point, HEp-3 attachment to both FN (FIG. 15A) and VN (FIG. 15B) was unaffected by the presence of either of the antimetastatic mAbs. Likewise, attachment of the overexpressing and weakly expressing HeLa transfectants to FN or VN was not blocked by mAb 50-6 or mAb 1A5. There was also no correlation between levels of PETA-3 expression and cell attachment. Similar results were obtained when the adhesion assays were terminated after 15 minutes, and when cell attachment was tested on plates coated with laminin, type I collagen and type IV collagen. These data indicate that PETA-3 is not functionally involved in cell attachment.

HEp-3 cells were tested for adhesion to Fibronectin (FN) in the presence of mAb 41-2 or normal mouse IgG. HEp-3 cells were added to the wells of 96-well plates coated with fibronectin in the presence of 50 μg/ml mAb 41-2 or normal mouse IgG, and incubated for various times as indicated. Non-adherent cells were gently washed away, and the amount of cell adhesion was determined by crystal violet staining. Data are expressed as the optical density (OD) at 595 nm of the incorporated crystal violet dye.

Figure 15C:
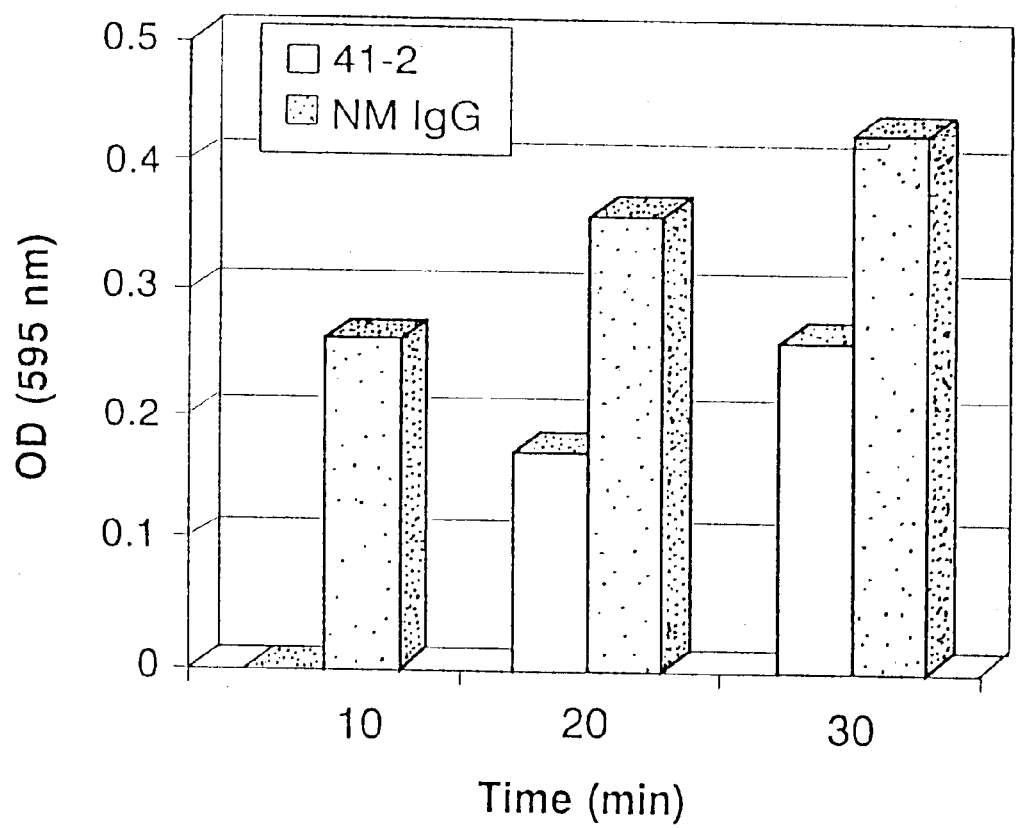
FIG. 15C depicts the effects of mAb 41-2 on cell adhesion of HEp-3 cells to fibronectin FIGS. 16A–16D graphically depict the in vivo angiogenesis assay.
Figure 16A:
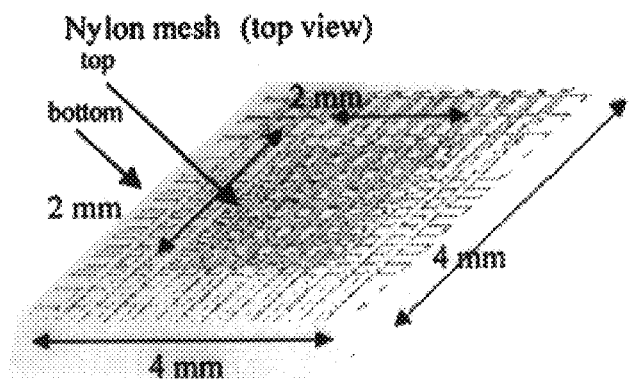
Figure 16B:
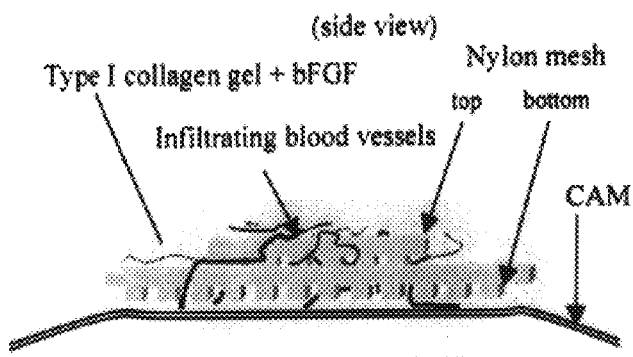
Figure 16C:
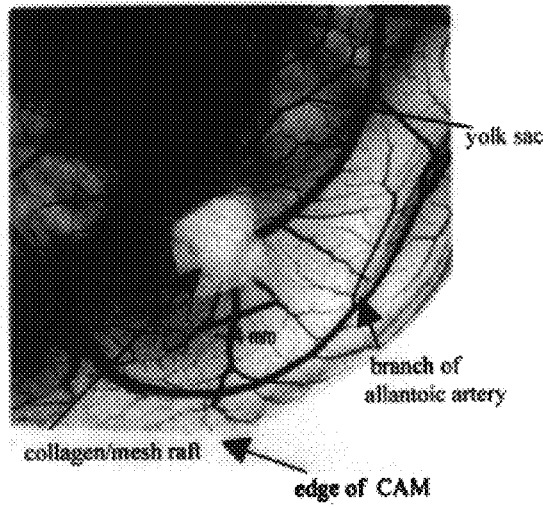
Figure 16D:
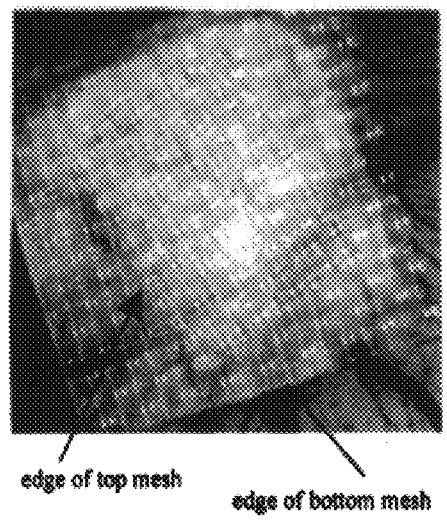

As shown in FIG. 15C, the inhibition of the HEp-3 attachment to FN by mAb 41-2 was 100% at the 10 minute time point, was about 53% at the 20 minute time point, and was about 38% at the 30 minute time point.

EXAMPLE 10

Inhibition of Growth-Factor Induced Angiogenesis by mAb 50-6

Collagen/mesh rafts which were used for angiogenesis assays were prepared in the following manner. Each raft was composed of an experimental or control collagen solution overlaid upon a single small nylon mesh placed above a single larger mesh. Nylon meshes (Tetko Nitex 3-180/43) were cut to 4 mm by 4 mm (hereafter referred to as "bottom mesh") and 2 mm by 2 mm (hereafter referred to as "top mesh") and sterilized by autoclaving. Purified type I collagen (3.1 mg/ml; Vitrogen) was neutralized on ice with addition of 10× phosphate-buffered saline (PBS), 1 N sodium hydroxide, and 1 M HEPES. Experimental or control solutions were prepared in PBS, including basic fibroblast growth factor at a final concentration of 16 µg/ml and bovine serum albumin at a final concentration of 1 mg/ml and kept on ice. Normal mouse IgG or mAb 50-6 were added to collagen solutions at a final concentration of either 50 or 100 µg/ml. Final collagen solutions were pipetted onto meshes, and rafts were placed in a 37.5° humidified incubator. After incubation for 45 minutes, rafts were ready for use in angiogenesis assays.

Just laid, pathogen-free fertile White Leghorn eggs were obtained from Spafas, Inc. and placed in a 42° C. humidified incubator on day 0. Sterile dishes and lids were prepared. Eggs were removed from the incubator on day 3, wiped with ethanol and shell contents were emptied into dishes using sterile technique. Thereafter, chicken embryos were maintained in a 37.5° humidified cell culture incubator. On day 8, embryos were removed from the incubator, collagen/mesh rafts prepared as described above were added. Each set of experiment typically included three control rafts (no growth factor, growth factor alone and growth factor together with the control antibody) and one experimental raft (growth factor plus experimental antibody). One of each raft was placed on the exposed chorioallantoic membrane of a separate 8 day-old chicken embryo. Embryos were returned to the incubator for an additional 64–66 hours (through day 11).

On day 11, embryos were removed from the incubator and examined under a Wild Heerbrugg M3 stereomicroscope at 90× magnification. The presence or absence of blood vessels at or above the plane of the top mesh was assessed for each box in the grid defined by the top mesh. The angiogenesis score was expressed as the fraction of boxes in top mesh containing vessels out of the total number of boxes in the top mesh. FIGS. 16A–16D graphically depict the angiogenesis assay.

Figure 17A:
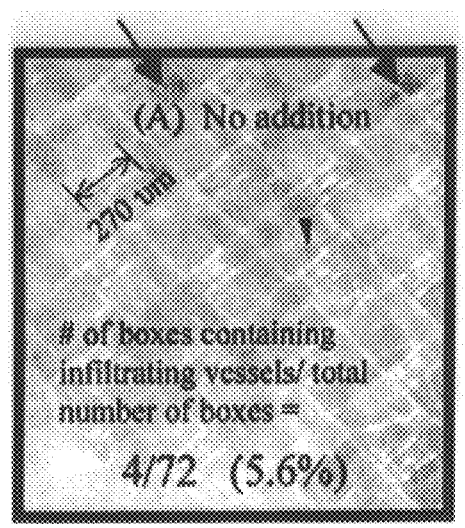
FIGS. 17A–17B depict the effect of bFGF on neovascularization of type I collagen matrix. Rafts are examined in situ after 66 hours incubation on the CAM using a dissecting microscope. Each box in the top mesh is scored as positive or negative based on the presence or absence of vessels that have penetrated up to the plane of the top mesh. (A) No addition and (B) bFGF (16 µg/ml). Arrowheads indicate representative nascent blood vessels in the plane of the top mesh. Selected vessels only are labeled.
Figure 17B:
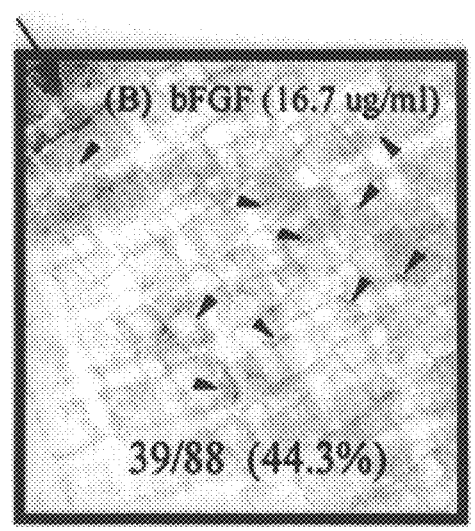
Figure 18:
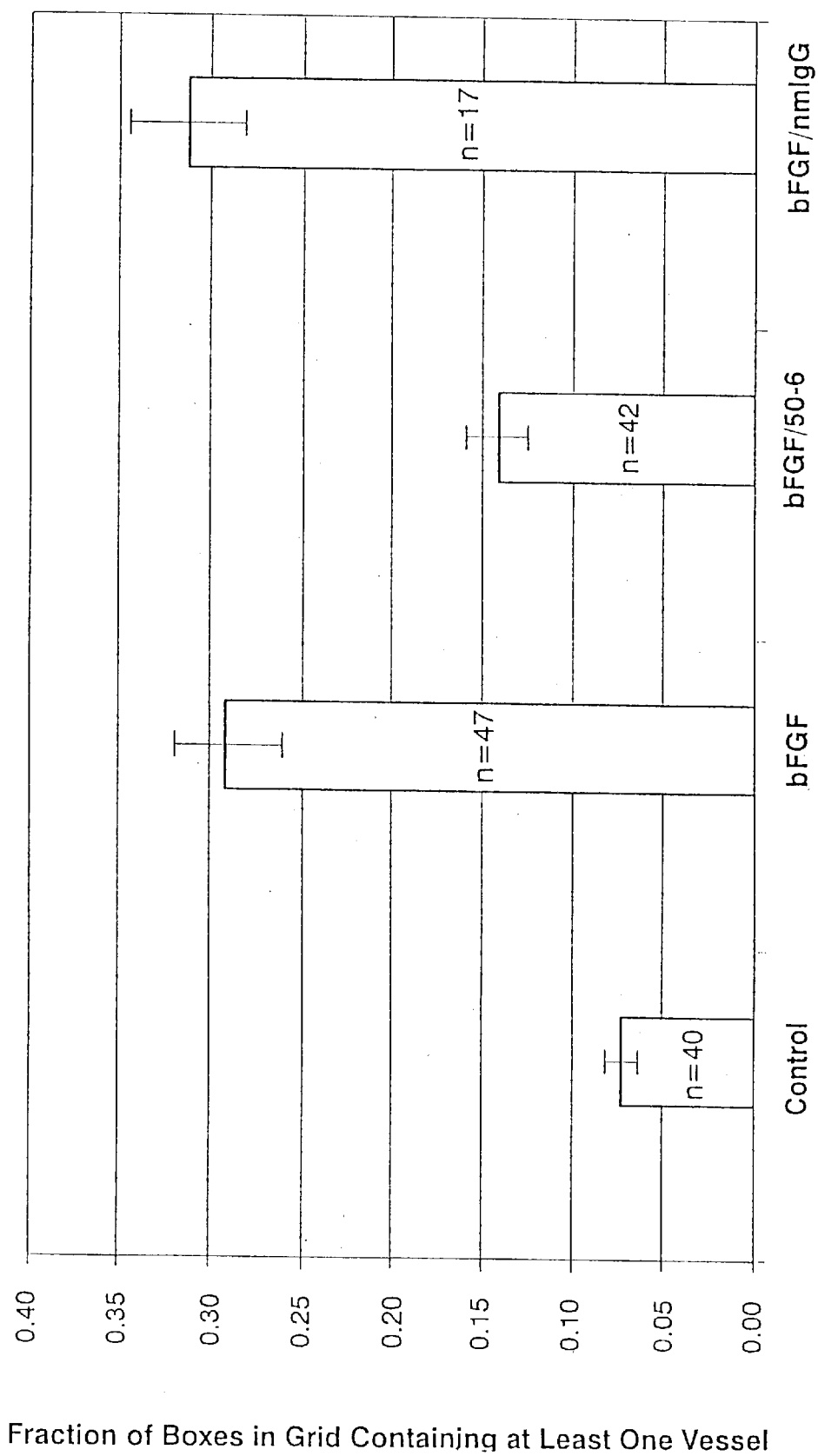
FIG. 18 depicts the effects of mAb 50-6 on basic fibroblast factor (bFGF)-induced angiogenesis on the chicken chorioallantoic membrane (CAM).

Basic fibroblast growth factor (bFGF) stimulates angiogenesis on the CAM (FIGS. 17A–18). However, the formation of new blood vessels is reduced by 55% in the presence of mAb 50-6 (FIG. 18). Control antibody (normal mouse IgG) had no effect on vessel formation. These results indicated that mAb 50-6 inhibited the function of its target antigen expressed by embryonic cells, and blocked the ability of these cells to form new vessels in response to bFGF.

EXAMPLE 11

Potential Functional Domains/Epitopes of PETA-3

Figure 19:
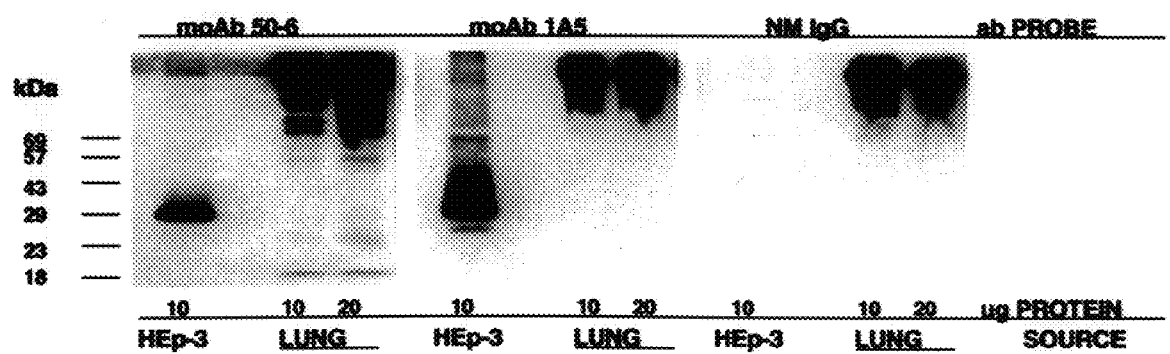
FIG. 19 depicts the Western Blot analysis of lysates of HEp-3 cells and normal mouse lung probed with mAb 50-6 and mAb1A-5. PETA-3 is seen at 29 kD in the HEp-3 lysates.

Both mAb 50-6 and mAb 1A5 were anti-functional and thus, it is proposed that the epitope(s) recognized by these antibodies represent a functional domain(s). Since neither mAb recognized the mouse homologue of PETA-3 (FIG. 19), the amino acid sequences of the mouse (SEQ ID NO: 4) and human (SEQ ID NO: 2) proteins were aligned to identify differences in the human sequence. As seen in FIG. 20, the small extracellular loop (amino acids 40–57, double underlined) contains only a single substitution, while in the large extracellular loop (amino acids 113–221, double underlined) there are a number of differences. Most of the changes are conservative. However, there are seven non-conservative substitutions (shaded in gray).

The epitope(s) recognized by mAb 50-6 and mAb 1A5 are conformational, since neither antibody recognized PETA-3 on Western blots of gels run under reducing conditions. The non-conservative substitutions in human PETA-3 could alter the conformation of the molecule relative to the mouse homologue, and are candidates for mutagenesis in order to identify the epitope(s) and/or functional domains of the protein.

The amino acid sequence of the large extracellular loop of human PETA-3 was also compared to human CD9 and CD63, two tetraspanins known to suppress metastasis (Hotta et al., *Melanoma Res.* 1: 125–132, 1991; Ikeyama et al., *J. Exp. Med.* 177: 1231–1237, 1993; Radford et al., *In. J. Cancer* 62: 631–635, 1995). As seen in FIG. 21, four of the seven non-conserved amino acid residues ($P^{137}$, $G^{176}$, $G^{177}$, and $Q^{194}$) identified in the comparison of mouse and human PETA-3 are absent in both of the other human tetraspanins, while the remaining three ($Q^{148}$, $R^{165}$, $Q^{173}$) are either missing or not well conserved in at least one of the other molecules. The alignment shown in FIG. 21 also shows that the overall homology between the large extracellular loops of these three proteins is poor and there are many regions of the PETA-3 molecule that would be appropriate for mutagenesis studies.

What is claimed is:

1. A method of diagnosing a metastatic tumor in a subject, comprising detecting the expression of the PETA-3 antigen with mAb 50-6 (ATCC#PTA-227), and determining a substantial increase of the expression of the antigen in the tissue being diagnosed compared with normal tissue.

2. A method of diagnosing a metastatic tumor in a subject, comprising detecting the expression of the PETA-3 antigen with a functional derivative of mAb 50-6 (ATCC#PTA-227), wherein said functional derivative comprises a Fab, Fab', or F(ab')$_2$ fragment of said antibody.

3. A method of diagnosing a metastatic tumor in a subject, comprising detecting the expression of the PETA-3 antigen with a functional derivative of mAb 50-6 (ATCC#PTA-227), wherein said functional derivative is a single chain antibody or a humanized antibody.

* * * * *

SEQUENCE LISTING

```
<160> NUMBER OF SEQ ID NOS:  5

<210> SEQ ID NO 1
<211> LENGTH: 870
<212> TYPE: DNA
<213> ORGANISM: Homo sapiens

<400> SEQUENCE: 1
```

```
atccactagt aacggccgcc agtgtggtgg aattcgagtc ctggggagct tctgtccacc    60
tgtcctgcag aggagtcgtt ccagcccgg ctgccccagg atgggtgagt caacgagaa    120 gaagacaaca tgtggcaccg tttgcctcaa gtacctgctg tttacctaca attgctgctt   180
ctggctggct ggcctggctg tcatggcagt gggcatctgg acgctggccc tcaagagtga   240
ctacatcagc ctgctggcct caggcaccta cctggccaca gcctcatcc tggtggtggc    300 gggcactgtc gtcatggtga ctggggtctt gggctgctgc gccaccttca aggagcgtcg   360
gaacctgctg cgcctgtact tcatcctgct cctcatcatc tttctgctgg agatcatcgc   420
tggtatcctc gcctacgcct actaccagca gctgaacacg gagctcaagg agaacctgaa   480
ggacaccatg accaagcgct accaccagcc gggccatgag gctgtgacca gcgctgtgga   540
ccagctgcag caggagttcc actgctgtgg cagcaacaac tcacaggact ggcgagacag   600
tgagtggatc cgctcacagg aggccggtgg ccgtgtggtc ccagacagct gctgcaagac   660
ggtggtggct ctttgtggac agcgagacca tgcctccaac atctacaagg tggagggcgg   720
ctgcatcacc aagttggaga ccttcatcca ggagcacctg agggtcattg gggctgtggg   780
gatcggcatt gcctgtgtgc aggtctttgg catgatcttc acgtgctgcc tgtacaggag   840
tctcaagctg gagcactact gaccctgcct                                    870
```

<210> SEQ ID NO 2
<211> LENGTH: 253
<212> TYPE: PRT
<213> ORGANISM: Homo sapiens

<400> SEQUENCE: 2

```
Met Gly Glu Phe Asn Glu Lys Lys Thr Thr Cys Gly Thr Val Cys Leu
 1               5                  10                  15

Lys Tyr Leu Leu Phe Thr Tyr Asn Cys Cys Phe Trp Leu Ala Gly Leu
            20                  25                  30

Ala Val Met Ala Val Gly Ile Trp Thr Leu Ala Leu Lys Ser Asp Tyr
        35                  40                  45

Ile Ser Leu Leu Ala Ser Gly Thr Tyr Leu Ala Thr Ala Tyr Ile Leu
    50                  55                  60

Val Val Ala Gly Thr Val Val Met Val Thr Gly Val Leu Gly Cys Cys
65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ile Ala Gly Ile Leu Ala Tyr
            100                 105                 110

Ala Tyr Tyr Gln Gln Leu Asn Thr Glu Leu Lys Glu Asn Leu Lys Asp
        115                 120                 125

Thr Met Thr Lys Arg Tyr His Gln Pro Gly His Glu Ala Val Thr Ser
    130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175

Gly Arg Val Val Pro Asp Ser Cys Cys Lys Thr Val Val Ala Leu Cys
            180                 185                 190

Gly Gln Arg Asp His Ala Ser Asn Ile Tyr Lys Val Glu Gly Gly Cys
        195                 200                 205

Ile Thr Lys Leu Glu Thr Phe Ile Gln Glu His Leu Arg Val Ile Gly
    210                 215                 220
```

```
Ala Val Gly Ile Gly Ile Ala Cys Val Gln Val Phe Gly Met Ile Phe
225                 230                 235                 240

Thr Cys Cys Leu Tyr Arg Ser Leu Lys Leu Glu His Tyr
            245                 250
```

<210> SEQ ID NO 3
<211> LENGTH: 19
<212> TYPE: PRT
<213> ORGANISM: synthetic construct
<220> FEATURE:
<221> NAME/KEY: UNSURE
<222> LOCATION: (15)
<223> OTHER INFORMATION: Xaa is Gln or Ile.
<221> NAME/KEY: UNSURE
<222> LOCATION: (17)

<400> SEQUENCE: 3

```
Phe Glu Ile Ala Leu Pro Arg Glu Ser Gln Ile Thr Val Leu Xaa Lys
 1               5                  10                  15

Xaa Gly Thr
```

<210> SEQ ID NO 4
<211> LENGTH: 253
<212> TYPE: PRT
<213> ORGANISM: Mus musculus

<400> SEQUENCE: 4

```
Met Gly Glu Phe Asn Glu Lys Lys Ala Thr Cys Gly Thr Val Cys Leu
 1               5                  10                  15

Lys Tyr Leu Leu Phe Thr Tyr Asn Cys Cys Phe Trp Leu Ala Gly Leu
                20                  25                  30

Ala Val Met Ala Val Gly Ile Trp Thr Leu Ala Leu Lys Ser Asp Tyr
            35                  40                  45

Ile Ser Leu Leu Ala Ser Ser Thr Tyr Leu Ala Thr Ala Tyr Ile Leu
     50                  55                  60

Val Val Ala Gly Val Val Met Val Thr Gly Val Leu Gly Cys Cys
 65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ile Ala Gly Ile Leu Ala Tyr
            100                 105                 110

Val Tyr Gln Gln Leu Leu Asn Thr Glu Leu Lys Glu Asn Leu Lys Asp
        115                 120                 125

Thr Met Val Lys Arg Tyr His Gln Ser Gly His Glu Gly Val Ser Ser
130                 135                 140

Ala Val Asp Lys Leu Gln Gln Glu Phe His Cys Cys Gly Ser Asn Asn
145                 150                 155                 160

Ser Gln Asp Trp Gln Asp Ser Glu Trp Ile Arg Ser Gly Glu Ala Asp
                165                 170                 175

Ser Arg Val Val Pro Asp Ser Cys Cys Lys Thr Met Val Ala Gly Cys
            180                 185                 190

Gly Lys Arg Asp His Ala Ser Asn Ile Tyr Lys Val Glu Gly Gly Cys
        195                 200                 205

Ile Thr Lys Leu Glu Thr Phe Ile Gln Glu His Leu Arg Val Ile Gly
    210                 215                 220

Ala Val Gly Ile Gly Ile Ala Cys Val Gln Val Phe Gly Met Ile Phe
225                 230                 235                 240
```

```
                        Thr Cys Cys Leu Tyr Arg Ser Leu Lys Leu Glu His Tyr
                                        245                 250
```

<210> SEQ ID NO 5
<211> LENGTH: 827
<212> TYPE: DNA
<213> ORGANISM: Homo sapiens
<220> FEATURE:
<221> NAME/KEY: CDS
<222> LOCATION: (57)..(815)

<400> SEQUENCE: 5

```
ggagcttctg tccacctgtc ctgcagagga gtcgtttcca gcccggctgc cccagg atg       59
                                                              Met
                                                                1 ggt gag ttc aac gag aag aag aca aca tgt ggc acc gtt tgc ctc aag        107
Gly Glu Phe Asn Glu Lys Lys Thr Thr Cys Gly Thr Val Cys Leu Lys
         5                  10                  15 tac ctg ctg ttt acc tac aat tgc tgc ttc tgg ctg gct ggc ctg gct        155
Tyr Leu Leu Phe Thr Tyr Asn Cys Cys Phe Trp Leu Ala Gly Leu Ala
     20                  25                  30 gtc atg gca gtg ggc atc tgg acg ctg gcc ctc aag agt gac tac atc        203
Val Met Ala Val Gly Ile Trp Thr Leu Ala Leu Lys Ser Asp Tyr Ile
 35                  40                  45 agc ctg ctg gcc tca ggc acc tac ctg gcc aca gcc tac atc ctg gtg        251
Ser Leu Leu Ala Ser Gly Thr Tyr Leu Ala Thr Ala Tyr Ile Leu Val
 50                  55                  60                  65 gtg gcg ggc act gtc gtc atg gtg act ggg gtc ttg ggc tgc tgc gcc        299
Val Ala Gly Thr Val Val Met Val Thr Gly Val Leu Gly Cys Cys Ala
                 70                  75                  80 acc ttc aag gag cgt cgg aac ctg ctg cgc ctg tac ttc atc ctg ctc        347
Thr Phe Lys Glu Arg Arg Asn Leu Leu Arg Leu Tyr Phe Ile Leu Leu
             85                  90                  95 ctc atc atc ttt ctg ctg gag atc atc gct ggt atc ctc gcc tac gcc        395
Leu Ile Ile Phe Leu Leu Glu Ile Ile Ala Gly Ile Leu Ala Tyr Ala
        100                 105                 110 tac tac cag cag ctg aac acg gag ctc aag gag aac ctg aag gac acc        443
Tyr Tyr Gln Gln Leu Asn Thr Glu Leu Lys Glu Asn Leu Lys Asp Thr
    115                 120                 125 atg acc aag cgc tac cac cag ccg ggc cat gag gct gtg acc agc gct        491
Met Thr Lys Arg Tyr His Gln Pro Gly His Glu Ala Val Thr Ser Ala
130                 135                 140                 145 gtg gac cag ctg cag cag gag ttc cac tgc tgt ggc agc aac aac tca        539
Val Asp Gln Leu Gln Gln Glu Phe His Cys Cys Gly Ser Asn Asn Ser
                150                 155                 160 cag gac tgg cga gac agt gag tgg atc cgc tca cag gag gcc ggt ggc        587
Gln Asp Trp Arg Asp Ser Glu Trp Ile Arg Ser Gln Glu Ala Gly Gly
            165                 170                 175 cgt gtg gtc cca gac agc tgc tgc aag acg gtg gtg gct ctt tgt gga        635
Arg Val Val Pro Asp Ser Cys Cys Lys Thr Val Val Ala Leu Cys Gly
        180                 185                 190 cag cga gac cat gcc tcc aac atc tac aag gtg gag ggc ggc tgc atc        683
Gln Arg Asp His Ala Ser Asn Ile Tyr Lys Val Glu Gly Gly Cys Ile
    195                 200                 205 acc aag ttg gag acc ttc atc cag gag cac ctg agg gtc att ggg gct        731
Thr Lys Leu Glu Thr Phe Ile Gln Glu His Leu Arg Val Ile Gly Ala
210                 215                 220                 225
```

-continued

```
gtg ggg atc ggc att gcc tgt gtg cag gtc ttt ggc atg atc ttc acg      779
Val Gly Ile Gly Ile Ala Cys Val Gln Val Phe Gly Met Ile Phe Thr
             230                 235                 240 tgc tgc ctg tac agg agt ctc aag ctg gag cac tac tgaccctgcc tt        827
Cys Cys Leu Tyr Arg Ser Leu Lys Leu Glu His Tyr
             245                 250
```